United States Patent
Wong et al.

(10) Patent No.: US 6,787,368 B1
(45) Date of Patent: Sep. 7, 2004

(54) BIOSENSOR METHOD FOR DETECTING ANALYTES IN A LIQUID

(75) Inventors: Wah Y. Wong, Edmonton (CA); Heman Chao, Edmonton (CA); Donald Segal, Stouffville (CA); Jerry McElroy, Richmond Hill (CA)

(73) Assignee: Helix BioPharma Corporation, Aurora (CA)

(*) Notice: Subject to any disclaimer, the term of this patent is extended or adjusted under 35 U.S.C. 154(b) by 0 days.

(21) Appl. No.: 09/517,597

(22) Filed: Mar. 2, 2000

Related U.S. Application Data

(60) Provisional application No. 60/122,548, filed on Mar. 2, 1999.

(51) Int. Cl.[7] .................. G01N 33/53; G01N 33/543
(52) U.S. Cl. .................. 436/518; 435/6; 435/7.1; 435/7.92; 435/174; 435/176; 435/287.1; 435/287.2; 435/288.7; 436/86; 436/164; 436/524; 436/527; 436/536; 349/1; 349/2; 349/33; 204/228.1; 204/229.8; 204/230.2; 204/400; 204/403; 204/406; 204/407; 204/409; 204/422
(58) Field of Search .................. 204/228.1, 229.8, 204/230.2, 400, 403, 406, 407, 409, 422; 349/1, 2, 33; 422/68.1; 435/4, 6, 7.1, 7.5, 7.92, 7.93, 174, 176, 287.1, 287.2, 288.7; 436/86, 164, 518, 524, 527, 536

(56) References Cited

U.S. PATENT DOCUMENTS

| | | | |
|---|---|---|---|
| 3,891,507 A | 6/1975 | Breuer | 195/103.5 R |
| 3,990,850 A | 11/1976 | Friedman et al. | 23/230 B |
| 4,038,030 A | 7/1977 | Albright et al. | 23/230 B |
| 4,789,804 A | 12/1988 | Karube et al. | 310/311 |
| 4,945,045 A | 7/1990 | Forrest et al. | 435/25 |
| 5,078,855 A | 1/1992 | Mochizuki et al. | 204/418 |
| 5,089,112 A | 2/1992 | Skotheim et al. | 204/403 |

(List continued on next page.)

FOREIGN PATENT DOCUMENTS

| | | |
|---|---|---|
| EP | 505 494 B1 | 7/1995 |
| WO | WO 89/01159 | 2/1989 |
| WO | WO 90/05303 | 5/1990 |
| WO | WO 93/15110 | 8/1993 |
| WO | WO 95/31480 | 11/1995 |
| WO | WO 96/02830 | 2/1996 |
| WO | WO 96/09547 | 3/1996 |
| WO | WO 96/10178 | 4/1996 |
| WO | WO 97/01092 | 1/1997 |
| WO | WO 97/02359 | 1/1997 |
| WO | WO 97/07593 | 2/1997 |
| WO | WO 97/41424 | 11/1997 |
| WO | WO 97/41425 | 11/1997 |
| WO | WO00/52456 | 9/2000 |

OTHER PUBLICATIONS

Hodges, R.S., "De novo design of α–helical proteins: basic research to medical applications," *Biochem. Cell Biol.* 74:133–154 (1996).

*Primary Examiner*—Long Le
*Assistant Examiner*—Kartic Padmanabhan
(74) *Attorney, Agent, or Firm*—Perkins Coie LLP

(57) ABSTRACT

A diagnostic method and device for use in detecting or quantitating an analyte present in a liquid sample. The method includes reacting an analyte-containing sample with reagents capable of generating a first coil-forming peptide in solution form. This peptide is then contacted with a biosensor whose detection surface has surface-bound molecules of a second, oppositely charged coil-forming peptide, under conditions effective to form a stable α-helical coiled-coil heterodimer on the detection surface. The formation of the coiled-coil heterodimer produces a measurable change in biosensor signal, which is measured to detect the presence of or quantitate the amount of analyte in a sample. Also disclosed is a biosensor device for carrying out the reaction.

10 Claims, 13 Drawing Sheets

U.S. PATENT DOCUMENTS

| | | | |
|---|---|---|---|
| 5,104,619 A | 4/1992 | de Castro et al. | 422/56 |
| 5,116,481 A | 5/1992 | Ozawa et al. | 204/290 R |
| 5,192,507 A | 3/1993 | Taylor et al. | 422/68.1 |
| 5,200,051 A | 4/1993 | Cozzette et al. | 204/403 |
| 5,242,828 A | 9/1993 | Bergström et al. | 435/291 |
| 5,246,846 A | 9/1993 | Pittner et al. | 435/174 |
| 5,268,305 A | 12/1993 | Ribi et al. | 436/501 |
| 5,313,264 A | 5/1994 | Ivarsson et al. | 386/73 |
| 5,368,712 A | 11/1994 | Tomich et al. | 204/403 |
| 5,401,378 A | 3/1995 | King et al. | 204/418 |
| 5,405,783 A | 4/1995 | Pirrung et al. | 436/518 |
| 5,436,161 A | 7/1995 | Bergström et al. | |
| 5,436,170 A | 7/1995 | Cornell et al. | 436/527 |
| 5,478,756 A | 12/1995 | Gizeli et al. | 436/527 |
| 5,485,277 A | 1/1996 | Foster | 356/445 |
| 5,491,097 A | 2/1996 | Ribi et al. | 436/518 |
| 5,492,840 A | 2/1996 | Malmqvist et al. | 436/518 |
| 5,514,501 A | 5/1996 | Tarlov | 430/5 |
| 5,527,711 A | 6/1996 | Tom-Moy et al. | 436/518 |
| 5,567,301 A | 10/1996 | Stetter et al. | 205/777.5 |
| 5,571,568 A | 11/1996 | Ribi et al. | 427/487 |
| 5,580,794 A | 12/1996 | Allen | 436/169 |
| 5,622,872 A | 4/1997 | Ribi | 436/518 |
| 5,624,537 A | 4/1997 | Turner et al. | 204/403 |
| 5,637,201 A | 6/1997 | Raguse et al. | 204/418 |
| 5,693,477 A | 12/1997 | Cornell et al. | 435/7.1 |
| 5,707,502 A | 1/1998 | McCaffrey et al. | 204/403.14 |
| 5,723,345 A | 3/1998 | Yamauchi et al. | 436/518 |
| 5,736,410 A | 4/1998 | Zarling et al. | 436/172 |
| 5,741,409 A | 4/1998 | Raguse et al. | 204/403.08 |
| 5,753,093 A | 5/1998 | Raguse et al. | 427/2.13 |
| 5,756,355 A | 5/1998 | Lang et al. | 435/7.21 |
| 5,783,054 A | 7/1998 | Raguse et al. | 204/403.08 |
| 5,798,030 A | 8/1998 | Raguse et al. | 204/403.08 |
| 5,824,483 A | 10/1998 | Houston, Jr. et al. | 435/7.1 |
| 5,834,224 A | 11/1998 | Ruger et al. | 205/777.5 |
| 5,942,388 A | 8/1999 | Willner et al. | 435/6 |
| 5,955,379 A | 9/1999 | Lennox et al. | 436/528 |
| 6,074,616 A | 6/2000 | Buechler et al. | 422/104 |
| 6,096,825 A | 8/2000 | Garnier | 525/54.1 |
| 6,107,080 A * | 8/2000 | Lennox | 204/228.1 |
| 6,165,335 A | 12/2000 | Lennox et al. | 204/403.01 |
| 6,300,141 B1 * | 10/2001 | Segal et al. | 204/228.1 |
| 6,461,490 B1 * | 10/2002 | Lennox et al. | 204/403.08 |
| 6,478,939 B1 * | 11/2002 | Lennox et al. | 204/403.08 |

* cited by examiner

BIOSENSOR METHOD FOR DETECTING ANALYTES IN A LIQUID

This application claims priority to U.S. Provisional Patent Application No. 60/122,548 filed Mar. 2, 1999, now pending, which is incorporated herein by reference.

FIELD OF THE INVENTION

The present invention relates to a method for detecting or quantitating an analyte, and to a biosensor for carrying out the method.

BACKGROUND OF THE INVENTION

Many tools used for detecting or quantitating biological analytes are based on analyte-specific binding between an analyte and an analyte-binding receptor or agent. Analyte/analyte binding pairs encountered commonly in diagnostics include antigen-antibody, hormone-receptor, drug-receptor, cell surface antigen-lectin, biotin-avidin, and complementary nucleic acid strands.

A variety of methods for detecting analyte-binding agent interactions have been developed. The simplest of these is a solid-phase format employing a reporter labeled analyte-binding agent whose binding to or release from a solid surface is dependent on the presence of analyte. In a typical solid-phase sandwich type assay, for example, the analyte to be measured is an analyte with two or more binding sites, allowing analyte binding both to a receptor, e.g., antibody, carried on a solid surface, and to a reporter-labeled second receptor. The presence of analyte is detected (or quantitated) by the presence (or amount) of reporter bound to solid surface.

In a typical solid-phase competitive binding analyte analog for binding to a receptor (analyte-binding agent) carried on a solid support. The amount of reporter signal associated with the solid support is inversely proportional to the amount of sample analyte to be detected or determined.

The reporter label used in both solid-phase formats is typically a visibly detectable particle or an enzyme capable of converting a substrate to an easily detectable product. Simple spectrophotometric devices allow for the quantitation of the amount of reporter label, for quantifying amount of analyte.

Detecting or quantitating analyte-specific binding events is also important in high-throughput methods being developed for combinatorial library screening. In a typical method, a large library of possible effector molecules (analytes) is synthesized. The library members are then screened for effector activity by their ability to bind to a selected receptor. The approach has the potential to identify, for example, new oligopeptide antigens capable of high-specificity binding to disease related antibodies, or small-molecule compounds capable of interacting with a selected pharmacological target, such as a membrane bound receptor or cellular enzyme.

High-throughput screening methods typically employ simple analyte displacement assays to detect and quantitate analyte binding to a receptor. Displacement assays have the advantage of high sensitivity, e.g., where the displaced analyte is radiolabeled, and also allow for the determination of analyte-receptor binding affinity, based on competitive displacement of a binding agent whose binding affinity to the target receptor is known.

In both diagnostics and high-throughput screening, there is increasing interest in developing biosensors capable of detecting and quantifying analyte-receptor binding events.

One general type of biosensor employs an electrode surface in combination with current or impedance measuring elements for detecting a change in current or impedance in response to the presence of a ligand-receptor binding event. This type of biosensor is disclosed, for example, in U.S. Pat. No. 5,567,301.

Gravimetric biosensors employ a piezoelectric crystal to generate a surface acoustic wave whose frequency, wavelength and/or resonance state are sensitive to surface mass on the crystal surface. The shift in acoustic wave properties is therefore indicative of a change in surface mass, e.g., due to a ligand-receptor binding event. U.S. Pat. Nos. 5,478,756 and 4,789,804 describe gravimetric biosensors of this type.

Biosensors based on surface plasmon resonance (SPR) effects have also been proposed, for example, In U.S. Pat. No. 5,485,277. These devices exploit the shift in SPR surface reflection angle that occurs with perturbations, e.g., binding events, at the SPR interface. Finally, a variety of biosensors that utilize changes in optical properties at a biosensor surface are known, e.g., U.S. Pat. No. 5,268,305.

The interest in biosensors is spurred by a number of potential advantages over strictly biochemical assay formats. First, biosensors may be produced, using conventional microchip technology, in highly reproducible and miniaturized form, with the capability of placing a large number of biosensor elements on a single substrate (e.g., see U.S. Pat. Nos. 5,200,051 and 5,212,050).

Secondly, because small signals can be readily amplified (and subjected to various types of signal processing if desired), biosensors have the potential for measuring minute quantities of analyte, and proportionately small changes in analyte levels.

A consequence of the features above is that a large number of different analytes can be detected or quantitated by applying a small sample volume, e.g., 10–50 $\mu$l, to a single multi-sensor chip.

Heretofore, electrochemical biosensors have been more successfully applied to detecting analytes that are themselves electrochemical species, or can participate in catalytic reactions that generate electrochemical species, than to detecting analyte-receptor binding events. This is not surprising, given the more difficult challenge of converting a biochemical binding event to an electrochemical signal. One approach to this problem is to provide two separate reaction elements in the biosensor: a first element contains a receptor and bound enzyme-linked analyte, and the second element, components for enzymatically generating and then measuring an electrochemical species. In operation, analyte displaces the analyte-enzyme conjugate from the first element, releasing the enzyme into the second element region, thus generating an electrochemical species which is measured in the second element.

Two-element biosensors of this type are relatively complicated to produce, particularly by conventional silicon-wafer methods, since one or more biological layers and permselective layers must be deposited as part of the manufacturing process. Further, enzymes or receptors in the biosensor can denature on storage, and the device may have variable "wetting" periods after a sample is applied.

Biosensors that attempt to couple electrochemical activity directly to an analyte-receptor binding event, by means of gated membrane electrodes, have been proposed. For example, U.S. Pat. Nos. 5,204,239 and 5,368,712 disclose gated membrane electrodes formed of a lipid bilayer membrane containing an ion-channel receptor that is either opened or closed by analyte binding to the receptor. Electrodes of this type are difficult to make and store, and are limited at present to a rather small group of receptor proteins.

Alternatively, direct analyte/receptor binding may be measured electrically by embedding the receptor in a thin polymer film, and measuring changes in the film's electrical properties, e.g., impedance, due to analyte binding to the receptors. U.S. Pat. No. 5,192,507 is exemplary. Since analyte binding to the receptor will have a rather small effect on film properties, and since no amplification effect is achieved, the approach is expected to have limited sensitivity.

PCT patent application PCT/CA97/00275, published Nov. 6, 1997, publication No. WO 97/41424, discloses a novel electrochemical biosensor having a conductive detection surface, and a hydrocarbon-chain monolayer formed on the surface. Biosensor operation is based on the flow of an ionized redox species across the monolayer, producing a measurable current flow. In one embodiment of the biosensor disclosed, binding of an analyte to its opposite binding member attached to the surface of some of the hydrocarbon chains increases measured current flow by increasing the disorder of the monolayer, making it more permeable to the redox species. In another general embodiment, the opposite binding member is anchored to the monolayer through a coiled-coil heterodimer structure, allowing any selected binding member carried on one (α-helical peptide to be readily attached to a "universal" monolayer surface carrying the opposite α-helical peptide.

The previously disclosed biosensor is capable of detecting and quantifying analyte-binding events and characterized by: (i) direct electrochemical conversion of the binding event to electrical signal; (ii) a high electron flow "turnover" from each binding event; (iii) adaptable to substantially any analyte, and (iv) good storage characteristics and rapid wetting with sample application.

Given these features, it would be desirable to improve the operational characteristics and suitability of the biosensor to a wide variety of analytes, as well as the adaptability of the biosensor to multianalyte formats, e.g., in a microfabricated form. The present invention is designed to provide these advantages.

SUMMARY OF THE INVENTION

The invention includes, in one aspect, a method for detecting or quantitating an analyte present in a liquid sample. The method includes reacting the liquid sample with an analyte-reaction reagent, thereby generating a solution form of a first coil-forming peptide having a selected charge and being capable of interacting with a second, oppositely charged coil-forming peptide to form a stable α-helical coiled-coil heterodimer.

The coil-forming peptide is contacted with a biosensor having a detection surface with surface-bound molecules of such second, oppositely charged coil-forming peptide, under conditions effective to form a stable α-helical coiled-coil heterodimer on the detection surface, where the binding of the solution form of the coil-forming peptide to the immobilized coil-forming peptide is effective to measurably alter a signal generated by the biosensor, which is measured to determine whether such coiled-coil heterodimer formation on said detector surface has occurred.

In one embodiment, the analyte is a ligand, and the reacting includes mixing the analyte with a conjugate of the first coil-forming peptide and the analyte or an analyte analog, and reacting the analyte and conjugate with an analyte-binding anti-ligand agent, such that the amount of unbound conjugate generated is inversely proportional to the amount of analyte. The analyte-bound agent is preferably immobilized. In another related embodiment, the conjugate is bound to the analyte-binding agent, and displaced from the binding agent in the presence of analyte.

In still another embodiment, the analyte is an enzyme and the reacting step is effective to enzymatically release the first coil-forming peptide in soluble form in the presence of analyte.

In one general embodiment, the biosensor is an electrochemical biosensor that includes a conductive detection surface, a monolayer composed of hydrocarbon chains anchored at their proximal ends to the detection surface, and the second charged coil-forming peptide also anchored to said surface, where the binding of the first peptide to the second peptide, to form such heterodimer, is effective to measurably alter current flow across the monolayer mediated by a redox ion species in an aqueous solution in contact with the monolayer, relative to electron flow observed in the presence of the second peptide alone.

Where the redox ion species has the same charge as said second coil-forming peptide, the binding of the first peptide to the second peptide is effective to enhance ion-mediated current flow across said monolayer. Where the redox ion species has a charge opposite that of said second coil-forming peptide, the binding of the first peptide to the second peptide is effective to reduce ion-mediated current flow across said monolayer.

In another aspect, the invention includes a diagnostic device for detecting or quantitating an analyte present in a liquid sample. The device includes a reaction reagent effective to react with analyte to generate a solution form of a first coil-forming peptide having a selected charge and being capable of interacting with a second, oppositely charged coil-forming peptide to form a stable α-helical coiled-coil heterodimer.

A biosensor in the device has a detection surface with surface-bound molecules of a second charged, coil-forming peptide capable of interacting with the first oppositely charged coil-forming peptide to form a stable α-helical coiled-coil heterodimer, where the binding of the first peptide to the second peptide, to form such heterodimer, is effective to measurably alter a signal generated by the biosensor, which is measured by a detector in the device.

The device may further include a substrate having formed therein (i) a sample-introduction region, (ii) the biosensor, and (iii) a sample-flow pathway between said sample-introduction region and the biosensor. The reaction reagent is disposed in the sample-flow pathway and includes a conjugate of the first coil-forming peptide and the analyte or an analyte analog, in a form releasable into the sample liquid, and an analyte-binding agent. The sample-flow pathway may include a mixing zone containing the conjugate in releasable form, and a reaction zone containing the analyte-binding agent in immobilized form.

The device also preferably includes a background control biosensor, and a control sample-flow pathway connecting the sample-introduction region to the background control biosensor, for measuring "baseline" current. The control sample-flow pathway lacks the analyte-conjugate.

In one general embodiment, the biosensor includes a conductive detection surface, a monolayer composed of hydrocarbon chains anchored at their proximal ends to the detection surface, and the second charged coil-forming peptide also anchored to the surface, where the binding of the first peptide to the second peptide, to form such heterodimer, is effective to measurably alter current flow across the monolayer mediated by a redox ion species in an aqueous solution in contact with the monolayer, relative to electron flow observed in the presence of the second peptide alone.

The redox ion species may have the same charge as the second coil-forming peptide, where the binding of the first peptide to the second peptide is effective to enhance redox ion-mediated current flow across the monolayer. Examples are the redox ion species is $Fe(CN)_6^{3-}$, if the charge of the second coil-forming peptide is negative, and $Ru(NH_3)_6^{3+}$, if the charge of the second coil-forming peptide is positive.

Alternatively, the redox ion species may have a charge opposite to that of the second coil-forming peptide, where the binding of the first peptide to the second peptide is effective to reduce ion-mediated current flow across said monolayer. Examples are $Fe(CN)_6^{3+}$, if the charge of the second coil-forming peptide is positive, and $Ru(NH_3)_6^{3+}$, if the charge of said second coil-forming peptide is negative.

In this general embodiment the electrode may have a gold detection surface and the monolayer may be composed of 8–22 carbon atom chains attached at their proximal ends to the detection surface by a thiol linkage, at a molecular density of about 3 to 5 chains/nm$^2$.

The device may be designed for use in detecting or quantitating a plurality of different selected analytes. Here the device includes, for each analyte, (i) a separate biosensor, and (ii) a separate sample-flow pathway connecting the sample-introduction region to each associated biosensor, where each sample-flow pathway includes (i) a conjugate of the first coil-forming peptide and one of the selected analytes or analog thereof, and (ii) an associated selected analyte-binding agent.

Preferably each biosensor in this embodiment contains substantially the same second charged, coil-forming peptide, and the sample-introduction region is a single port communicating with each of the sample-flow pathways. The sample introduction region, biosensors, and sample-flow pathways may be microfabricated on the substrate.

These and other objects and features of the invention will become more fully apparent when the following detailed description of the invention is read in conjunction with the accompanying drawings.

DETAILED DESCRIPTION OF THE INVENTION

Figure 1A:
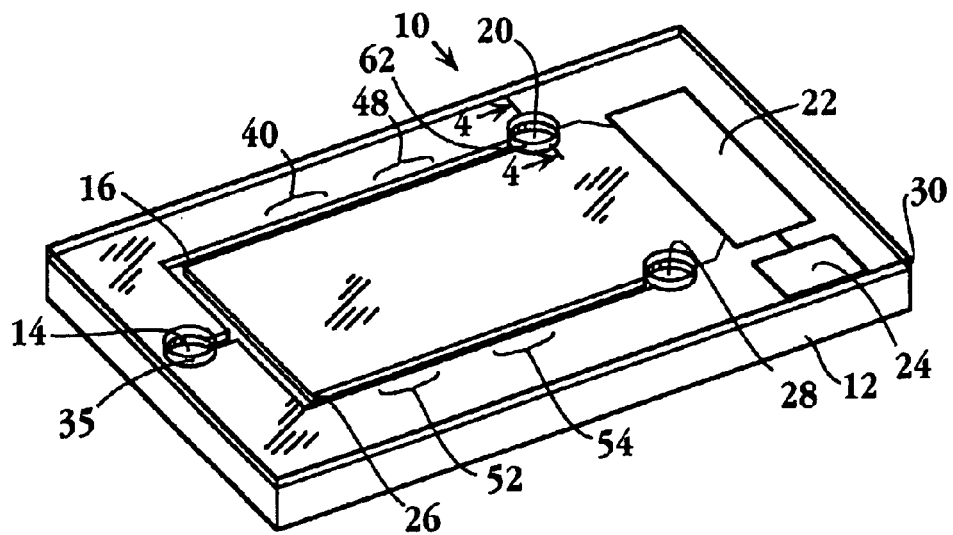
FIG. 1A is a simplified, partly schematic perspective view of a microfabricated substrate used in a single-analyte detection device in accordance with one aspect of the invention.

FIG. 1A is a simplified perspective view of a diagnostic device 10 in accordance with one embodiment of the present invention. The apparatus includes a substrate 12, sample introduction region 14, sample-flow pathway 16, biosensor 20, and a detector for measuring a change in a signal generated by the biosensor 22. The device optionally includes a signal-responsive element for recording the output signal, e.g., a visually readable output 24. Details of each element are further described hereinbelow. The device preferably includes a control sample-flow pathway 26 and background control biosensor 28.

Before proceeding further with the description of the specific embodiments of the present invention, a number of terms will be defined.

"Analyte" is defined as the compound or composition to be measured, which is a member of a specific binding pair (sbp) and may be a ligand, which is mono- or poly-valent, usually antigenic or haptenic, a single or plurality of compounds which share at least one common epitopic or determinant site, or a receptor.

"Analyte-binding agent" is defined as any compound or composition capable of recognizing a particular spatial and polar organization of an analyte molecule, e.g., epitopic or determinant site. The device of the present invention can be used in detecting the presence or amount in a sample of an analyte which forms with an analyte-binding agent, an analyte-analyte-binding agent pair. Non-limiting examples of such pairs include antigen-antibody, hormone-receptor, drug-receptor, cell surface carbohydrate-lectin, biotin-avidin, and complementary nucleic acids. Numerous examples of such pairs are known (e.g., as described in U.S. Pat. No. 5,716,778 (1998) to Ullman).

"Analyte analog" is defined as a modified analyte which can compete with the analogous analyte for a receptor, the modification providing means to join an analyte analog to another molecule.

"Bibulous material" is defined as a porous material having pores of at least 0.1 $\mu$m, preferably at least 1.0 $\mu$m, which is susceptible to traversal by an aqueous medium in response to capillary force. Such materials are generally hydrophilic or are capable of being rendered hydrophilic and include inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, etc.; either used by themselves or in conjunction with other materials; ceramic materials; and the like. The bibulous material can be attached to a support. The bibulous material may be polyfunctional or be capable of being polyfunctionalized to permit covalent bonding of compounds as described hereinbelow.

Binding of molecules to the bibulous material may be accomplished by well-known techniques, commonly available in the literature. See, for example, "Immobilized Enzymes," Ichiro Chibata, Halsted Press, New York (1978) and Cuatrecasas, et al, J. Bio. Chem., 245:3059 (1970).

The bibulous material can be a single structure such as a sheet cut into strips or it can be particulate material bound to a support or solid surface. In a preferred embodiment, the material is applied using a screen printing technique, such as described in U.S. Pat. No. 5,736,188.

The substrate 12 is a generally planar solid support for the device, preferably composed of an electrically insulating, non-porous, rigid, moisture impermeable material. A wide variety of organic and inorganic materials, both natural and synthetic, and combinations thereof, may be employed provided only that the support does not interfere with the capillary action of the bibulous material, or non-specifically bind assay components, or interfere with the signal producing system. Illustrative polymers include polyethylene, polypropylene, poly(4-methylbutene), polystyrene, polymethacrylate, poly(ethylene terephthalate), nylon, poly (vinyl butyrate), glass, and ceramics. The device preferably includes a cover 30 which can be transparent.

The sample introduction region 14 provides a site for application of a liquid sample containing analyte 34 (FIGS. 2A–2B, 3A–3B). As used herein, "liquid sample" typically refers to a naturally occurring or artificially formed liquid test medium suspected of containing the analyte of interest. The liquid sample may be derived from a wide variety of sources such as physiologic fluid illustrated by blood, serum, plasma, urine, ocular lens fluid, saliva, amniotic and spinal fluid, etc., food products such as milk or wine, chemical processing streams, or waste water, etc. The volume of sample can vary between 1–200 $\mu$L. In a preferred embodiment, the sample introduction region is an inlet port which is in liquid communication with the with sample flow pathway 16.

The sample-flow pathway 16 is a channel or conduit between the sample-introduction region 14 and the biosensor 20. In one embodiment, the sample-flow pathway is an essentially unblocked passage of a diameter suitable for conveying the liquid sample from the sample introduction region 14 to the biosensor 20. Such a microfluidic trench can be formed by micromachining substrate material, e.g., as described in U.S. Pat. No. 5,194,133 or by injection molding. Liquid sample migrates in the sample flow pathway by capillary action or can be driven by a micro-pump or by electroosmosis. As described hereinbelow, assay reagents are bound either in a releasable form or immobilized within the pathway 16. For example, the reagents can be bound to the walls of the pathway 16. In a preferred embodiment, along the length of the sample-flow pathway 16 is an insoluble bibulous material 38 for conveying the sample by capillarity and for binding assay reagents either in a releasable form or an immobilized form.

Figure 2A:
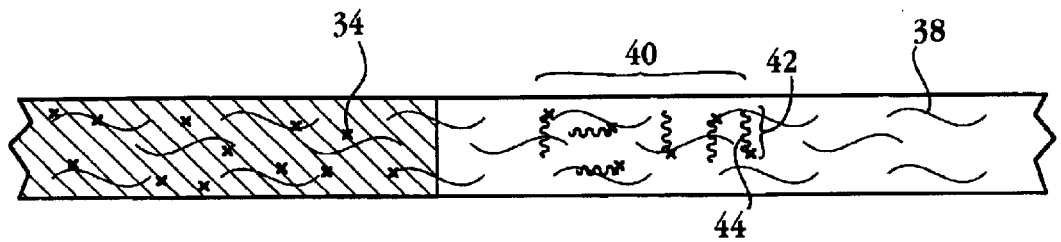
FIG. 2A is a partly schematic view of the mixing zone in a biosensor device.
Figure 2B:
FIG. 2B is a partly schematic view of the mixing zone in a biosensor device indicating the migration of test sample as a cross-hatched area.
Figure 3A:
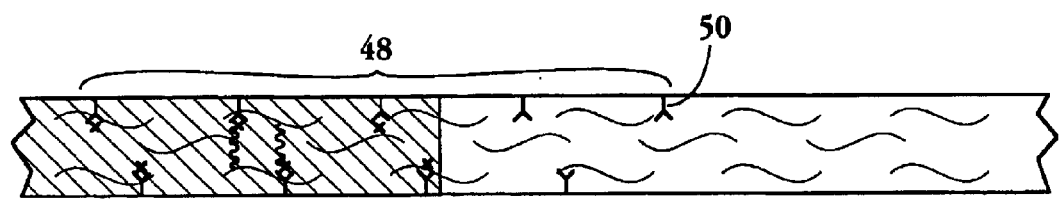
FIG. 3A is a partly schematic view of the reaction zone in a biosensor device.
Figure 3B:
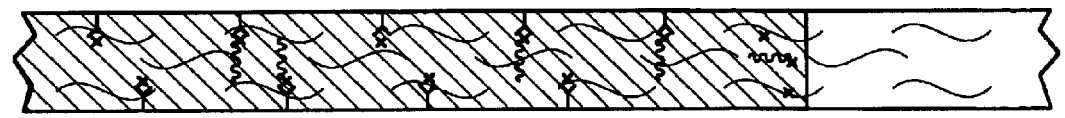
FIG. 3B is a partly schematic view of the reaction zone in a biosensor device indicating the migration of test sample as a cross-hatched area.

Downstream of the sample introduction region 14, the sample flow-pathway includes a mixing zone 40 as shown in FIG. 1A and FIGS. 2A–2B. The mixing zone contains a conjugate 42 consisting of the analyte (or analyte analog) 34 linked to a charged coil-forming peptide 44. Peptide 44 is selected for forming a heterodimer with an oppositely charged coil-forming peptide which is anchored within the biosensor 20, as described hereinbelow. Conjugate 42 is provided in mixing zone 40 in a form which is releasable, i.e., diffusible, into the sample liquid when sample is drawn, e.g., by capillarity, into the mixing zone. For example, conventional methods are used for releasably binding the conjugate to the bibulous material, such as the spot and dry method as described in U.S. Pat. No. 5,580,794 (which is incorporated by reference in its entirety herein) or using an applicator such as the Bio Dot dispenser (Bio Dot, Inc. Irvine, Calif.).

Downstream of the mixing zone 40 is reaction zone 48 (FIG. 1A and FIGS. 3A–3B) in which analyte-binding agent 50 is immobilized within the pathway 16. In one embodiment, the analyte-binding agent is an antibody to the analyte. The immobilization of proteins onto glass and other surfaces, are known (e.g., as discussed in U.S. Pat. No. 5,192,507, which is incorporated by reference in its entirety herein). Immobilization of molecules to a bibulous material is performed using conventional methods such as a soak and dry immobilization method, or by immobilizing the protein to latex microparticles of about 5–20 $\mu$mm and drawing these modified microparticles into the membrane matrix using vacuum pressure.

During the passage of liquid sample through the reaction zone 48, analyte 34 and conjugate 42 react with the binding agent 50 under conditions effective to immobilize analyte or conjugate so bound to the binding agent In a preferred embodiment of the invention, the device further includes a control sample-flow pathway 26, in liquid communication with the sample introduction region 14 and a background control biosensor 28. Preferably, the control sample-flow pathway lacks the conjugate in the control mixing zone, but is otherwise similar to the sample-flow pathway 16.

It will be appreciated from the discussion hereinabove that due to competitive binding in reaction zone 48, there will be an inverse relationship between the amount of analyte in a liquid sample and the amount of conjugate 42 bound in zone 48. Sample liquid flowing downstream from zone 48 contains conjugate 42 not bound in zone 48. Thus, there is a positive relationship between the level of conjugate in the liquid sample liquid emerging downstream from zone 48 and the level of analyte in the original liquid sample. The amount of reagents, such as binding agent 50 and conjugate 42, provided within the sample-flow pathway is predetermined by optimization methods well known in the art. For example, in the absence of analyte, the amount of binding agent 50 in zone 48 preferably is just sufficient to bind all of conjugate 42.

In general, the biosensor of the invention has a detection surface with surface-bound molecules of a second charged, coil-forming peptide capable of interacting with a first oppositely charged coil-forming peptide to form a stable alpha-helical coiled-coil heterodimer. The two oppositely charged peptides spontaneously self-assemble into a heterodimer complex. In one embodiment, the invention employs an electrochemical biosensor which measures current flow across a hydrocarbon-chain monolayer, anchored to the detector surface, mediated by redox species in aqueous solution in contact with monolayer relative to electric flow observed in the absence of analyte-peptide conjugate. Other embodiments employ a gravimetric biosensor, a surface plasmon resonance biosensor, or an optical biosensor, as described hereinbelow.

In a general embodiment of the invention, a second charged coil-forming peptide 46 is anchored to the biosensor surface. A first charged coil forming peptide 44 is linked to analyte (or analog) as a conjugate 42. The peptides 44 and 46 form a heterodimer and are two non-identical, preferably oppositely charged polypeptide chains, typically each about 21 to about 70 residues in length, having an amino acid sequence compatible with their formation into stable two-stranded α-helical heterodimeric coiled-coils. They are designated herein as HSP1 (heterodimer-subunit peptide 1), and HSP2 (heterodimer-subunit peptide 2). In the discussion below, HSP1 will refer to the peptide attached to the biosensor surface in the biosensor, and HSP2, to the peptide having an attached analyte. It will be understood that these designations refer to the functional role played by the subunit peptide, not the actual peptide sequence.

Figure 1B:
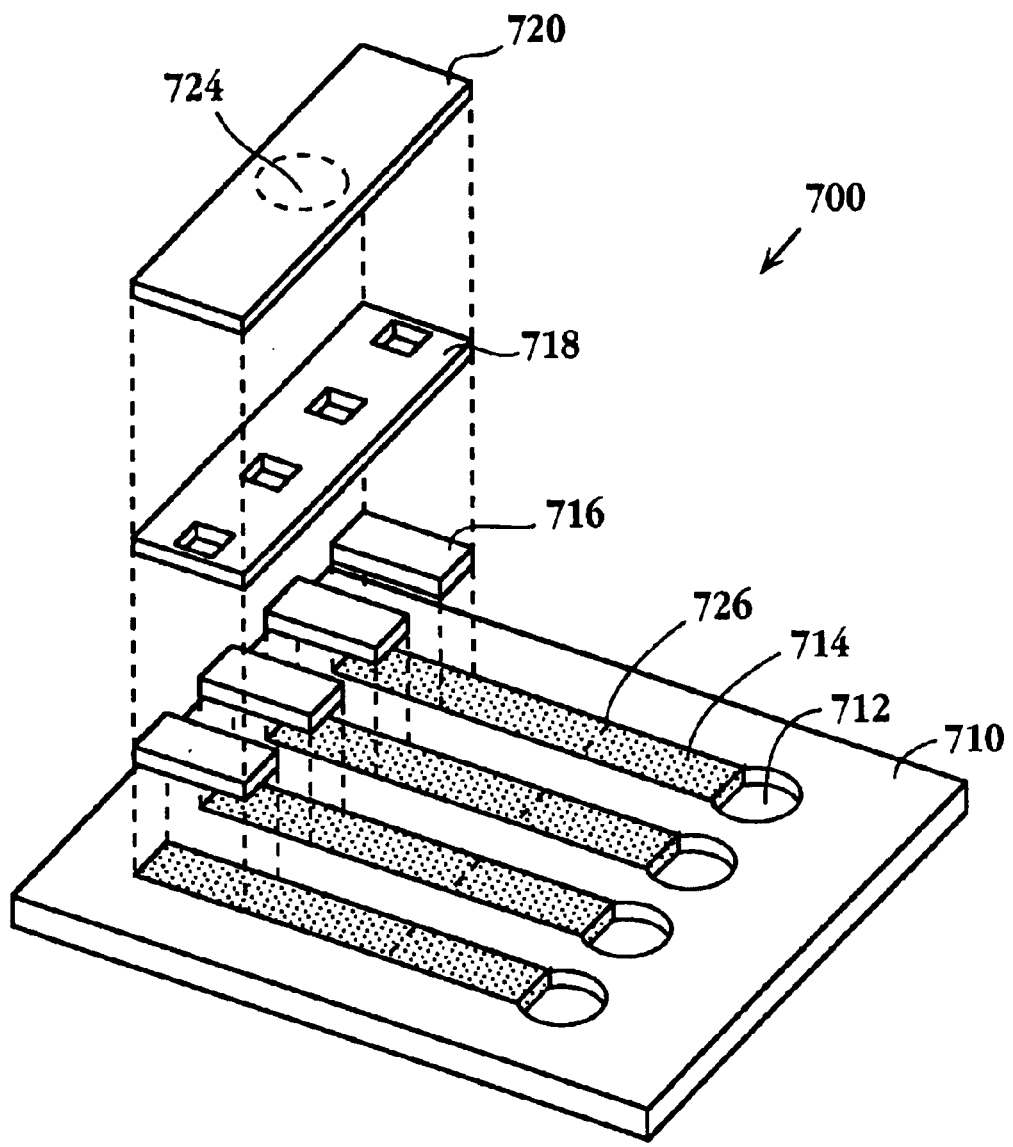
FIG. 1B is an exploded view of an embodiment of a detection device in accordance with the invention.

Another embodiment of the invention is shown in FIG. 1B. In analogy with device 10, the device 700 includes a substrate 710, biosensor 712, sample flow path 714 comprising a bibulous material, aconjugate pad 716, a plastic (e.g., polyurethane) spacer 718, and filter element 720. The conjugate pad, comprising a bibulous matrix, contains diffusively bound conjugate. The flow path 714 comprises a bibulous matrix containing non-diffusively bound analyte binding agent. Sample introduced at a sample application area 724 permeates the filter 720 which serves to remove particulate matter, such as cells. Spacer 718 facilitates the distribution of the fluid flowing from filter 720 into pad 716. The fluid mixes with HSP2/analyte conjugate in pad 716 and enters matrix 714 which includes a mixing zone 726. The fluid emerging from the matrix 514 enters biosensor 712 as described hereinabove. The device preferably includes a background control biosensor and a positive control biosensor in analogy with device 250 described herein.

Figure 1C:
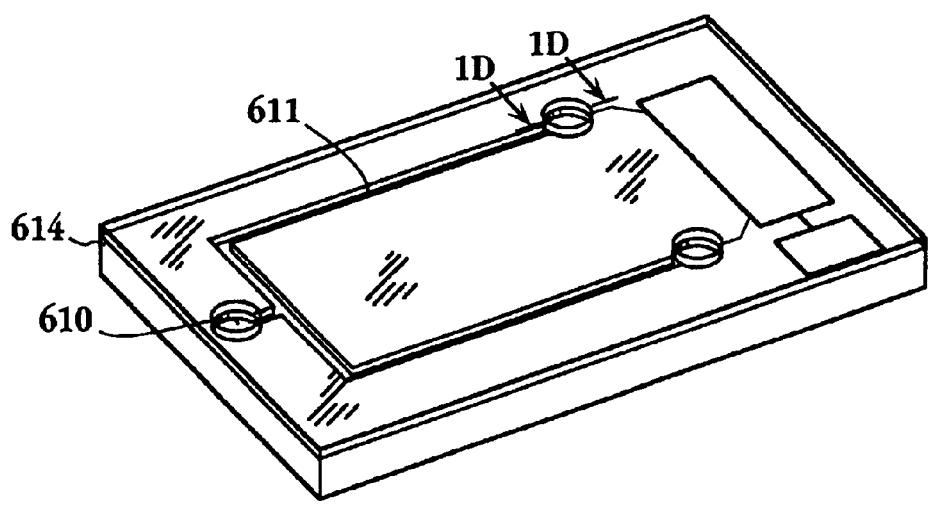
FIG. 1C is a simplified, partly schematic perspective view of another embodiment of a device in accordance with the invention.
Figure 1D:
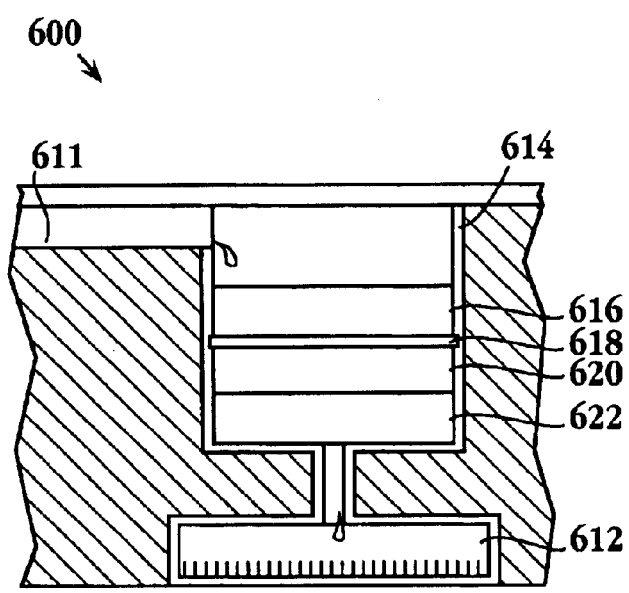
FIG. 1D is a schematic and enlarged diagram of a side view of a section of the device of FIG. 1C taken along the arrows 1D.

Yet another embodiment of the device 600 is shown in FIGS. 1C, 1D. The device 600 includes a housing 614, sample application port 610, microchannel 611, biosensor chamber 612, filter element 616, porous support element 618, conjugate pad 620, and matrix element 622. Sample introduced at port 610 enters the top of the device permeates the filter 616 which serves to remove particulate matter, such as cells. The conjugate pad 620 contains diffusively bound conjugate. Matrix 622 comprises a bibulous matrix containing non-diffusively bound analyte binding agent. Support element 618 supports the filter 616 and has openings therethrough for downward transfer, under the influence of gravity and also capillary action, of fluid from filter 616 into conjugate pad 620. The fluid mixes with HSP2/analyte conjugate in pad 620 and enters matrix 622. The fluid emerging from the matrix 622 enters biosensor 612. A plurality of separate biosensors can be arranged, preferably on a planar on a substrate, to receive sample fluid delivered from microchannels emanating from a central sample application area (FIG. 1C). The device preferably includes a background control biosensor and a positive control biosensor in analogy with device 250 described herein.

The devices of the present invention can include filters which can include means for sample pre-treatment, such as filtering red blood cells (U.S. Pat. Nos. 5,658,444; 5.837, 546; 5,747,274). The filters can comprise separation material such as synthetic membranes, fibrous depth filters such as glass fiber, plastic fiber, metal fiber, cellulose fiber or any combination of filters and membranes. The separation material may be untreated or can be coated with protein, dextran, sugars, or carbohydrates for red cell stabilization, LDL, precipitation reagents such as magnesium chloride and dextran sulfate, antibodies or red cell agglutination agents to facilitate red cell removal. Sample pretreatment within a filter can also adjust the pH to within a specific range, reference salt concentration, turbidity and or viscosity, and/ or reduce or remove interfering substances such as immunochemical cross-reactants, redox substances and the like.

Figure 4:
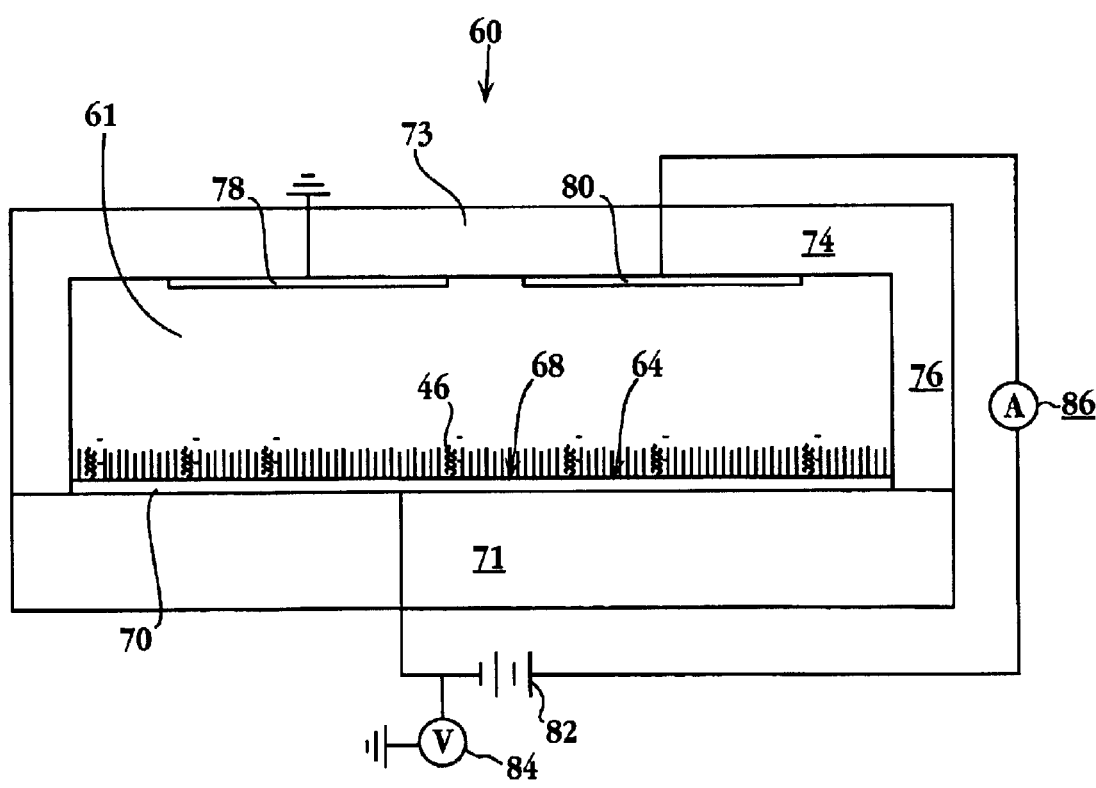
FIG. 4 is a cross-sectional view taken in the direction of arrows 4—4 in FIG. 1A of an amperometric biosensor constructed in accordance with one embodiment of the invention.

FIG. 4 shows a simplified schematic view of an electrochemical biosensor 60 for detecting an analyte-peptide quantitating conjugate in a liquid medium, in accordance with the invention. The biosensor includes a chamber 61 that is in liquid communication with the sample-flow pathway of the device via opening 62. Although not shown, the chamber may include a second port or vent to facilitate liquid flow through the port. The biosensor 60 includes a working electrode 64 having a conductive detection surface 66, and, in a preferred embodiment, a hydrocarbon-chain monolayer 68 formed on the detection surface. In the embodiment shown, the detection surface is the upper surface of a conductive film 70 deposited on substrate 71. Details of the monolayer formed on the detection surface, and the method of forming the monolayer on the surface, are discussed below.

A cover 73 in the apparatus has an upper wall 74, and side walls, such as wall 76, which are joined to edge regions of the substrate to form a closed chamber 61 therewith. The chamber serves to hold an aqueous solution required for biosensor operation, as will be described.

A reference electrode 78 and a counter electrode 80 in the apparatus are provided on the chamber-facing surface of wall 74, as shown, and are thus both in conductive contact with electrode 64 when the chamber is filled with an electrolyte solution. In the device of the invention, the sample liquid enters the chamber through an opening such as shown at 62 downstream from the mixing zone. In a preferred embodiment, electrolyte reagents are provided within the chamber preferably in a dry form that is readily dissolved within the sample fluid. For example, reagents can be lyophilized and deposited, or spotted and dried, in the reaction zone or in the sample flow pathway as described in U.S. Pat. No. 5,580,794. The liquid entering the chamber mixes with ionic species capable of undergoing a redox reaction, ie., losing or gaining an electron, at a suitably charge electrode. Exemplary redox species are $Fe(CN)_6^{3-/4-}$, as a negatively charged species, and $Ru(NH_3)_6^{2+/3+}$ as a positively charged species. Other probes which can be used include $Mo(CN)_6^{3-}$ ($E_0$=+800 mV), $W(CN)_6^{3-}$ ($E_0$=+580 mV), $Fe(CN)_6^{4-}$ ($E_0$=+580 mV), $Ce^{4+/3+}$, ($E_0$=+1.4V), and $Fe^{+3/2+}$ ($E_0$=+666 mV). Typical redox ion concentrations are between 0.01 and 10 mM. The solution is contained in chamber 60 and is in contact with reference and counter electrodes.

The voltage potential placed on the electrode, i.e., between the electrode and reference electrode, is typically at least 90 mV above the electrochemical potential ($E_0$) value of the redox species, for oxidation, and at least 90 mV below the electrochemical potential, for reduction of the species. Consider, for example, $Fe(CN)_6^{3-/4-}$, with an $E_0$ of 450 mV (vs. NHE). Above about 550 mV electrode potential, any $Fe^{2+}$ species is oxidized to $Fe^{3+}$, and at an electrode potential below about 350 mV, and $Fe^{+3}$ is reduced to $Fe^{+2}$. Similarly, $Ru(NH_3)_6^{2+/3+}$ has an $E_0$ of +50 mV (vs. NHE), so oxidation is achieved at an electrode potential above about +150 mV, and reduction, below about −50 mV.

The reference electrode 78, which is held at ground, serves as the voltage potential reference of the working electrode 64 when a selected potential is placed on the working electrode by a voltage source 82. This potential is measured by a voltage measuring device 84 which can additionally include conventional circuitry for maintaining the potential at a selected voltage, typically between about −500 to +800 mV.

Voltage source 82 is connected to counter electrode 80 through a current measuring device 86 as shown, for measuring current flow between the two electrodes during biosensor operation. The reference and counter electrodes are Pt, Ag, Ag/AgCl, or other suitable electrodes. The reference and working electrodes, the circuitry connecting them to the working electrode, and voltage source, are referred to herein, collectively, as means for measuring ion-mediated electron flow across the working-electrode monolayer, in response to heteroduplex formation between HSP2-analyte conjugate and a charged, coil-forming peptide HSP1 46 anchored to the surface 66 of the working electrode 64.

Figure 5A:
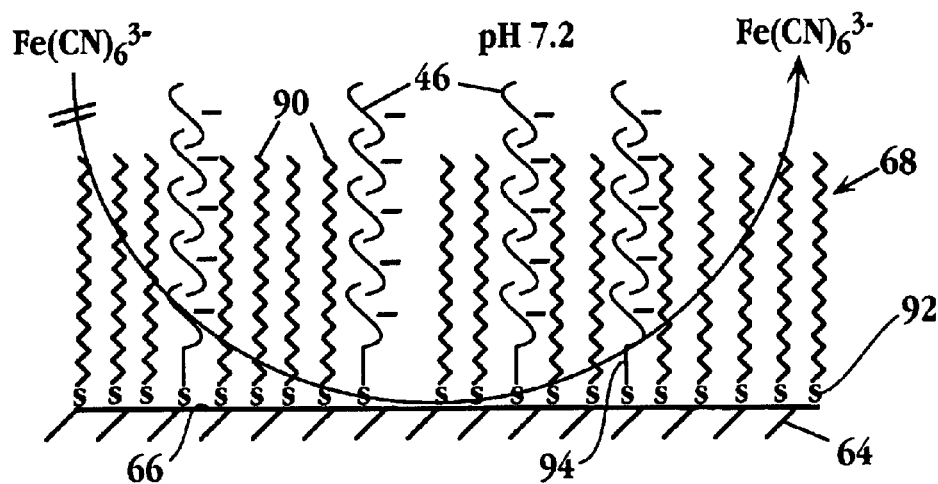
FIG. 5A is an enlarged view of a region of the electrode in the biosensor shown in FIG. 4.
Figure 5B:
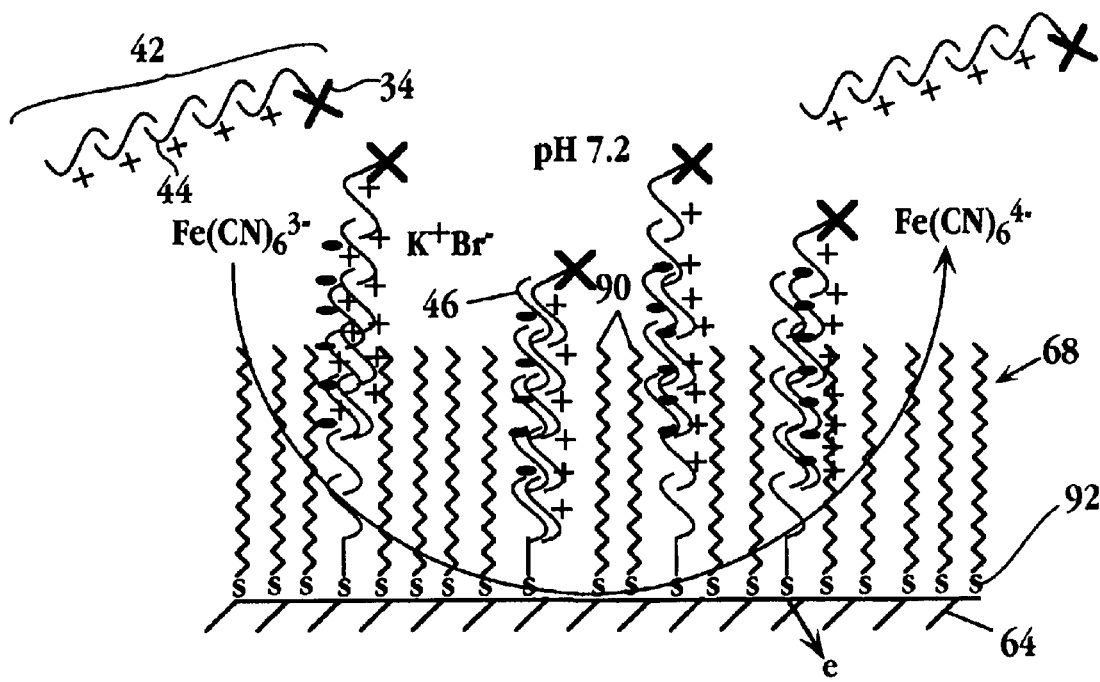
FIG. 5B is an enlarged view of a region of the electrode in the biosensor shown in FIG. 4, in the presence of HSP2-analyte conjugate.

FIGS. 5A–5B are an enlarged view of a portion of the working electrode 64 having a conductive detection surface 66 and a hydrocarbon-chain monolayer 68 formed on the detection surface. The chains forming the monolayer are typically 8–22 carbon, saturated hydrocarbon chains, although longer chains, chains with some unsaturation, chains with non-carbon chain atoms, such as lipid ethers, and/or chains with minor branching, such as by non-chain methyl groups, may be employed, within the constraint that the chains, at a sufficient packing density, form a sufficiently close packed and ordered monolayer to be effective as a barrier to electron flow, under biosensor operating conditions, as discussed below. This density is calculated to be between 3–5 chains/nm$^2$.

In the embodiment shown in FIGS. 5A–5B, the chains 90 are coupled to the electrode detecting surface through sulfhydryl linkages 92, although other suitable coupling groups may be employed. One method for producing monolayers having suitable hydrocarbon chain densities is passive diffusion of chains onto the surface of an electrode. A preferred method consists of actively driving the chains onto the surface by applying a positive voltage potential to the conductor surface. The latter method achieves rapid monolayer formation and highly reproducible electrode characteristics.

In a preferred embodiment of the invention, the hydrocarbon-chain mixture which is actively driven onto the conductor surface includes peptide HSP1 peptide 46 that is capable of forming a stabilized, alpha-helical peptide heterodimer with an oppositely charged, complementary subunit, HSP2. Such heterodimer subunits are described in PCT patent application WO 95/31480 "Heterodimer Polypeptide Immunogen Carrier Composition and Method", publication date 23 Nov. 1995, which is incorporated herein by reference. Exemplary subunits are referred to herein as K-coils, referring to positively charged subunits whose charge is provided dominantly by lysine residues, and E coils, referring to negatively subunits whose charge is provided dominantly by glutamic acid residues.

HSP1 peptide 46 can be attached to the distal end of a short hydrocarbon chain (end opposite the chain's thiol group) by suitable lipid-to-peptide conjugation, e.g., by ester linkage to a hydrocarbon fatty acid. Alternatively, the peptide may be linked to the electrode surface through a peptide spacer, e.g., a tripeptide spacer that extends from one end of the subunit and includes cysteine as a terminal residue, for sulfhydryl attachment to the electrode surface. In both cases, the modified peptide is mixed with the hydrocarbon chains, at a selected mole ratio, then driven into a monolayer formation by applying a positive voltage to the electrode, resulting in a densely packed hydrocarbon-chain monolayer 68 which includes charged, coil-forming peptide 46 embedded in the planar chain matrix, while still retaining a low dielectric barrier to ion flow through the monolayer. The HSP1 peptide 46 is included in the monolayer in a mole ratio peptide/hydrocarbon chains of preferably between 1:100 to 1:5.

In a preferred method for forming the monolayer, a mixture of thiol-containing chains and thiol-terminated HSP1 peptide, at a selected mole ratio, is actively driven to the surface by applying a positive voltage potential to the substrate surface, e.g., gold film. In practice, the hydrocarbon chain mixture (about 1 mM hydrocarbon chains) in an ethanolic solution of 100 mM Li perchlorate, neutral pH, is placed over the electrode, and a selected potential is applied to the electrode. The buildup of the monolayer can be monitored by increase in layer thickness. Alternatively, monolayer formation is monitored by measuring current across the monolayer, as described below. In this case, formation of the monolayer will be characterized by a steady drop in electrode current, until minimum current is reached, at which point maximum chain packing has been achieved.

Active deposition of the C16 and peptide subunit can be carried out sequentially in addition to the mixed mode, or simultaneous deposition, described hereinabove. The conditions for the sequential deposition are essentially the same except that the peptide subunit is deposited first and the C16 subsequently.

The time required to achieve saturation packing density will vary with applied voltage, and can be as short as 10 seconds—about 4 orders of magnitude faster than monolayer formation by diffusion. Complete or nearly complete monolayer formation (30 Å thickness) occurs within 10 minutes at about 1V potential and above. At lower positive voltages, additional reaction time is required. Preferably the voltage applied to the electrode is at least between about +250 mV relative to a normal hydrogen electrode (+250 vs. NHE) and 1.2V (vs. NHE).

Not only are rapid monolayer formation times achieved, but the percentages of peptide and hydrocarbon chains present in the reaction mixture are precisely represented in the monolayers, giving highly reproducible electrode characteristics.

In aqueous medium, the isolated heterodimer-subunit peptides are typically random coils. When HSP1 and HSP2 are mixed together under conditions favoring the formation of α-helical coiled-coil heterodimers, they interact to form a two-subunit α-helical coiled-coil heterodimeric complex. Peptides in an α-helical coiled-coil conformation interact with one another in a characteristic manner that is determined by the primary sequence of each peptide. The tertiary structure of an α-helix is such that 7 amino acid residues in the primary sequence correspond to approximately 2 turns of the α-helix. Accordingly, a primary amino acid sequence giving rise to an α-helical conformation may be broken down into units of 7 residues each, termed heptads. The heterodimer-subunit peptides are composed of a series of heptads in tandem. When the sequence of a heptad is repeated in a particular heterodimer-subunit peptide, the heptad may be referred to as a "heptad repeat", or simply "repeat".

The dimerization of HSP1 and HSP2 is due to the presence of a repeated heptad motif of conserved amino acid residues in each peptide's primary amino acid sequence. Repeating heptad motifs having appropriate amino acid sequences direct the HSP1 and HSP2 polypeptides to assemble into a heterodimeric α-helical coiled-coil structure under permissible conditions. The individual α-helical peptides contact one another along their respective hydrophobic faces.

HSP1 and HSP2 may assemble into a heterodimer coiled-coil helix (coiled-coil heterodimer) in either parallel or antiparallel configurations. In a parallel configuration, the two heterodimer-subunit peptide helixes are aligned such that they have the same orientation (amino-terminal to carboxyl-terminal). In an antiparallel configuration, the helixes are arranged such that the amino-terminal end of one helix is aligned with the carboxyl-terminal end of the other helix, and vice versa.

Heterodimer-subunit peptides designed in accord with the guidance presented in the above-referenced PCT application typically show a preference for assembling in a parallel orientation vs. an antiparallel orientation. For example, the exemplary peptides identified by SEQ ID NO:1 and SEQ ID NO:2, form parallel-configuration heterodimers as do other peptide sequences (as discussed in the PCT application). When attaching an analyte to HSP2, it is generally desirable to attach the analyte at or near the end of the peptide that will form the distal end of the heterodimer. In particular, where the heterodimer forms a parallel configuration, the HSP1 peptide is preferably anchored to the biosensor surface at its C terminus, and the analyte conjugated to the HSP2 peptide at its N terminus.

As just noted, one of the two subunit peptides (HSP1) in the heterodimer is anchored to the biosensor surface, and the second peptide (HSP2) contains an analyte intended to participate in a binding reaction in the reaction zone of the device. In both cases, the peptide is synthesized, or derivatized after synthesis, to provide the requisite attachment function and analyte, respectively.

Considering the modification of HSP1, the peptide may be synthesized, at either its N or C terminus, to carry additional terminal peptides that can function as a spacer between the biosensor surface and the helical-forming part of the peptide. Alternatively, the HSP1 peptide can be attached to the biosensor surface thorough a high-affinity binding reaction, such as between a biotin moiety carried on the peptide and an avidin molecule covalently attached to the surface.

Where HSP1 is embedded in a hydrocarbon-chain monolayer (FIGS. 5A–5B) the spacer anchoring the HSP1 peptide to the biosensor surface may be a hydrocarbon chain. The chain is preferably a fractional length of the chains making up the bilayer, such that the distal ends of the heterodimer which forms upon binding of the two peptides in the assembled monolayer are at or near the exposed surface of the monolayer. Thus, for example, if the monolayer is made up of 18-carbon chains, the spacer is preferably 2–10 carbons in length, depending on the length of the heterodimer.

The hydrocarbon-chain spacer, in the form of a omega-thio fatty acid, may be coupled to a terminal hydroxyl or amine coupling during solid-phase synthesis, as outlined above. The derivatized peptide, in turn, can be attached to a metal surface by standard thiolate coupling (Dakkouri, et al., Langmuir (1996) 12:2849–2852).

Where the analyte is a polypeptide, the analyte can be synthesized by either solid-state or recombinant methods, to include the peptide analyte at the end of the HSP2 peptide that will orient distally in the assembled heterodimer. Where the analyte is a non-peptide moiety, e.g., a non-peptide hormone, drug, or nucleic acid, the HSP2 peptide can be synthesized to include one or more residues that can be specifically derivatized with the analyte. In forming the conjugate, such as 42, the analyte is preferably covalently attached to the N-terminal amino acid residue, or to one of the residues facing the exposed face of the heterodimer. Preferred coupling groups are the thiol groups of cysteine residues, which are easily modified by standard methods. Other useful coupling groups include the thioester of methionine, the imidazolyl group of histidine, the guanidinyl group of arginine, the phenolic group of tyrosine and the indolyl group of tryptophan. These coupling groups can be derivatized using reaction conditions known to those skilled in the art.

To bind the analyte-HSP2 conjugate 42 to the surface-immobilized HSP1 peptide 46, the two peptides are contacted under conditions that favor heterodimer formation. A medium favoring coiled-coil heterodimer formation is a physiologically-compatible aqueous solution typically having a pH of between about 6 and about 8 and a salt concentration of between about 50 mM and about 500 mM. Preferably, the salt concentration is between about 100 mM and about 200 mM. An exemplary benign medium has the following composition: 50 mM potassium phosphate, 100 mM KCl, pH 7. Equally effective media may be made by substituting, for example, sodium phosphate for potassium phosphate and/or NaCl for KCl. Heterodimers may form under conditions outside the above pH and salt range, medium, but some of the molecular interactions and relative stability of heterodimers vs. homodimers may differ from characteristics detailed above. For example, ionic interactions between the ionic groups that tend to stabilize heterodimers may break down at low or high pH values due to the protonation of, for example, Glu side chains at acidic pH, or the deprotonation of, for example, Lys side chains at basic pH. Such effects of low and high pH values on coiled-coil heterodimer formation may be overcome, however, by increasing salt concentration.

Increasing the salt concentration can neutralize the stabilizing ionic attractions or suppress the destabilizing ionic repulsions. Certain salts have greater efficacy at neutralizing the ionic interactions. For example, in the case of the K-coil peptide 44 in FIG. 5A, a 1M or greater concentration of $ClO_4^-$ anions is required to induce maximal α-helical structure, whereas a 3M or greater concentration of $Cl^-$ ions is required for the same effect. The effects of high salt on coiled-coil formation at low and high pH also show that interhelical ionic attractions are not essential for helix formation, but rather, control whether a coiled-coil tends to form as a heterodimer vs. a homodimer.

FIGS. 5A–5B show a biosensor electrode 64 in which the hydrocarbon chain monolayer 68 includes an E-coil peptide subunit, such as subunit 46, as described above. In the embodiment shown, each peptide subunit is coupled to the electrode surface via a tripeptide spacer, such as spacer 94 in subunit 46, which is itself attached to the electrode surface through a sulfhydryl linkage, as shown. The peptide, including the peptide spacer, is formed conventionally, e.g., by solid phase synthesis. The monolayer was formed according to the method described above.

Because of the negative charge imparted to the monolayer by the E coil subunits 46, the monolayer shows relatively low conductance to negatively charged redox species, such as $Fe(CN)_6^{3-}$, as evidenced by a relatively low oxidation or reduction current with the redox species.

FIG. 5B shows the same monolayer, but after addition of complementary, positively charged K-coil subunits 44 conjugated to analyte, such as indicated at 42. As shown, oppositely charged subunits pair to form charge-neutral heterodimers in the monolayer.

Without wishing to be bound by theory, in the absence of heteroduplex formation between the two charged coiled peptides, the monolayer retains its net negative charge, forming an effective barrier to electron flow across the monolayer mediated by a redox ion species of the same charge, when a suitable oxidizing or reducing potential is placed across the monolayer. This is reflected by a low measured current across the membrane. With binding of an analyte-HSP2 conjugate to an anchored HSP1 in the monolayer, the repulsive negative of the monolayer is reduced sufficiently to allow the movement of redox species through the monolayer, producing electron flow through the electrode. The biosensor records this binding event as an increase in current across the electrode, i.e., between the working and counter electrodes. It will be recognized that the peptide used for HSP1 can have a negative or positive charge, but that the preferred redox ion has the same charge as HSP1. Thus, in an alternative embodiment of this aspect of the invention, HSP1 can be a K-coil, and a redox species of the same charge can be used, e.g., $Ru(NH_3)_6^{6+}$, with a negatively charged HSP2 used in the conjugate.

By analogy to a transistor, the redox solution serves as the "source", the monolayer as the "gate", and the underlying electrode as the "drain". Current flow in a transistor is initiated by applying a threshold voltage to the gate. In the biosensor of the invention, current flow is initiated by a stimulus—in this case, heteroduplex formation—to the monolayer "gate".

Figure 6:
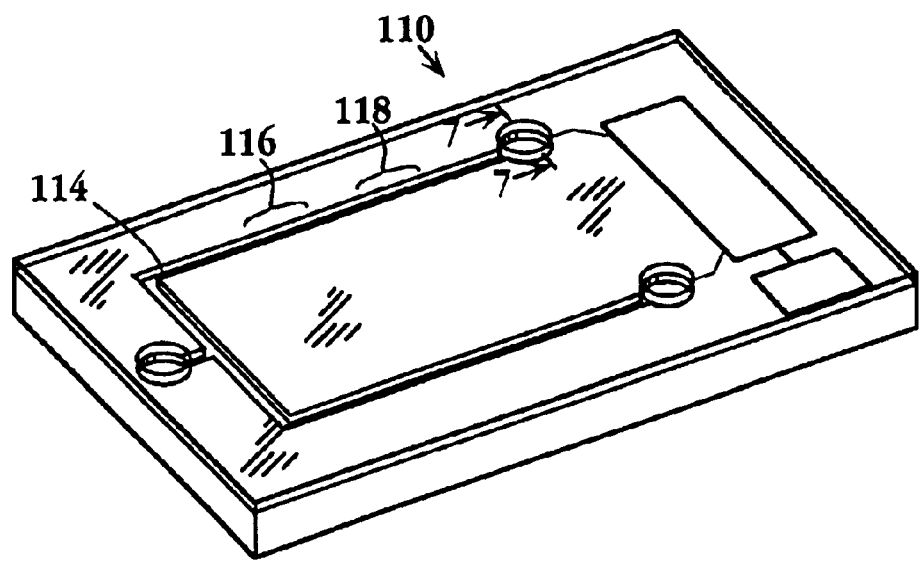
FIG. 6 is a simplified, partly schematic perspective view of a microfabricated substrate used in a Pseudomonas PAK pilin peptide-detection device in accordance with one aspect of the invention.
Figure 7A:
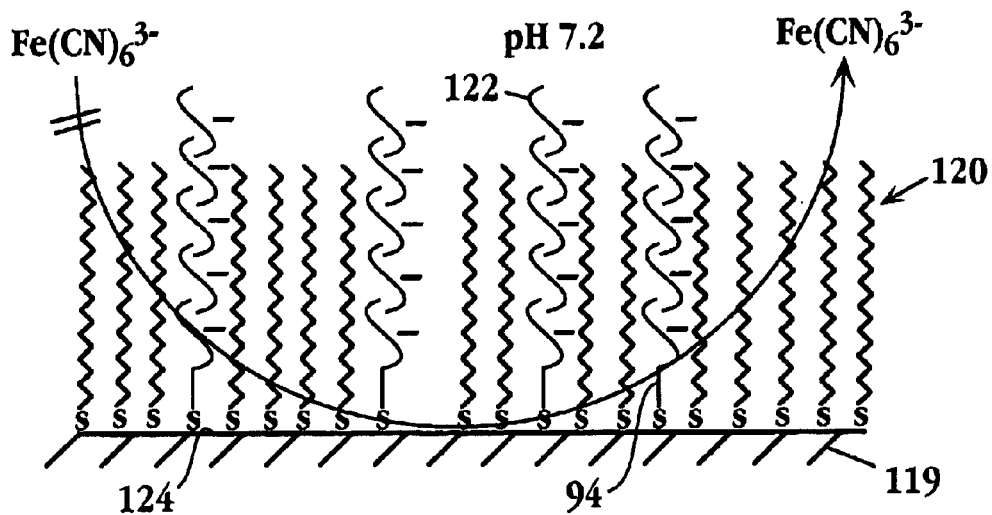
FIG. 7A is an enlarged view of a region of the electrode in the biosensor shown in FIG. 6 taken in the direction of arrows 7—7.
Figure 7B:
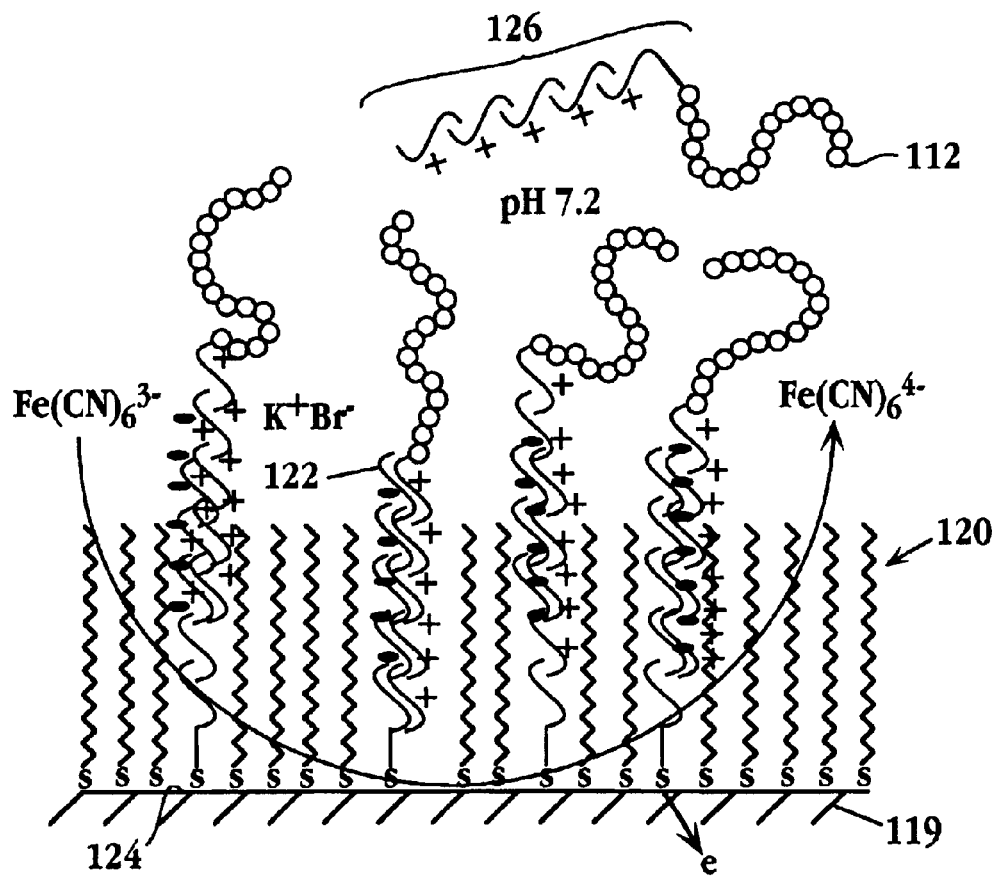
FIG. 7B is an enlarged view of a region of the electrode in the biosensor shown in FIG. 6 taken in the direction of arrows 7—7, in the presence of HSP2-PAK peptide conjugate.

FIGS. 6 and 7A–7B show a diagnostic device 110 for detection and quantitation of Pseudomonas PAK pilin peptide 112 constructed in accordance with the invention. The sample flow pathway 114 of the device contains a polystyrene-divinylbenzene matrix and has a mixing zone 116 containing a conjugate of HSP2-PAK peptide bound in a releasable form. Binding zone 118 contains (16-thiohydroxy)hexadecanyl O-(2-acetamido-2-deoxy-β-D-galactopyranosyl(1□4)-D-galacopyranoside immobilized to the bibulous material through the 16 thiol moiety (not shown). This disaccharide is specifically reactive with PAK peptide, forming a ligand-receptor pair with the peptide.

FIGS. 7A–7B show a magnified view of the biosensor electrode 119 of device 110 which includes a hydrocarbon monolayer 120 with embedded HSP1 122 covalently attached to the electrode surface 124. The biosensor electrode was prepared as described with reference to FIG. 5A, employing a ratio of non-HSP1 to HSP1-chains of about 4 to 1. FIGS. 7A and 7B show HSP1 before and after binding of an HSP2-PAK conjugate 126, respectively.

Figure 8A:
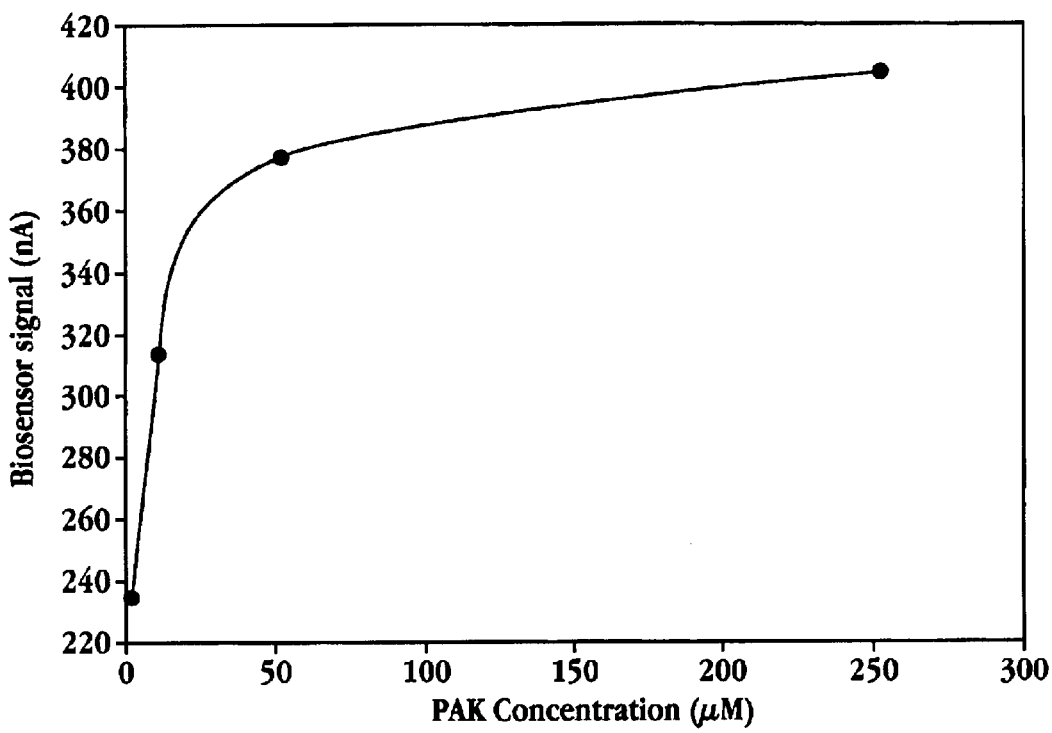
FIGS. 8A and 8B are idealized linear (8A) and semilog (8B) plots showing change in biosensor signal, measured in nA, as a function of PAK pilin peptide added to the biosensor device, where the second α-helical peptide has the same charge as the redox ion species.
Figure 8B:
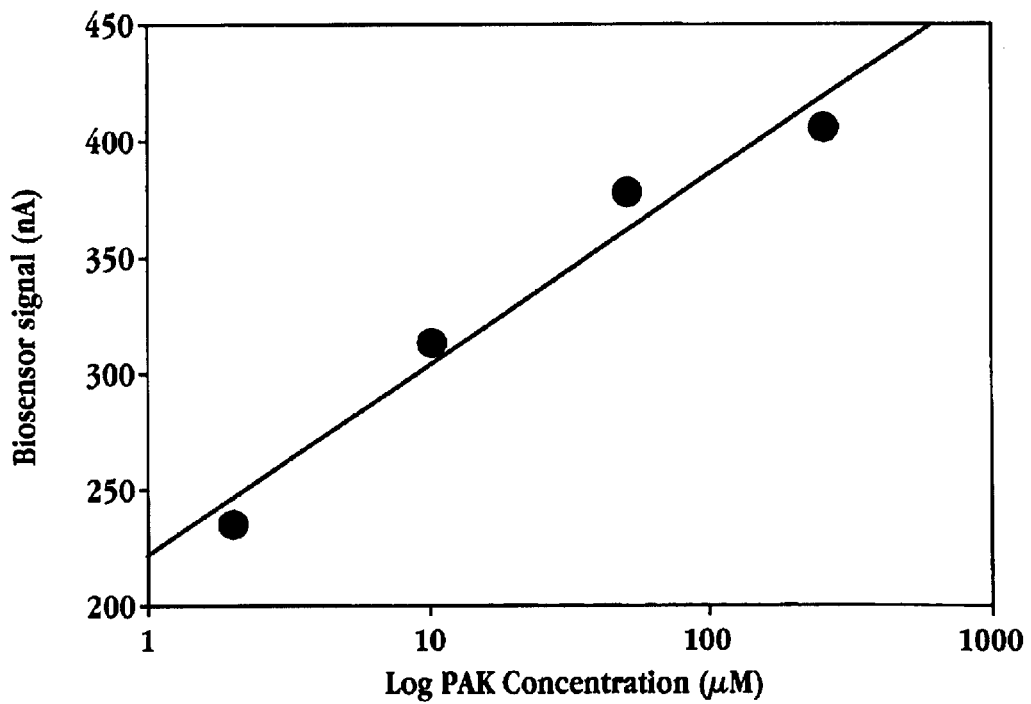

The operating response of the biosensor is illustrated in FIGS. 8A–8B. An increase in Pseudomonas PAK protein receptor in the test sample produces an increase in biosensor signal. The signal increases by about 2-fold, from 225 nA to 400 nA, over a concentration range of 0 to 250 μM PAK in the test sample.

Figure 15:
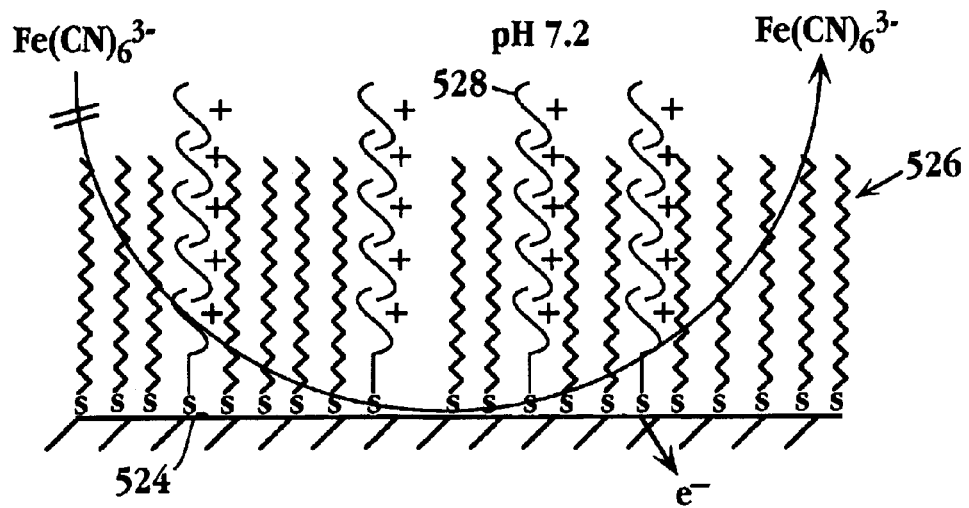
FIG. 15 illustrates the structure of an electrode monolayer having an embedded K-coil peptide subunit.

FIG. 15 shows a biosensor electrode 524 in which the hydrocarbon chain monolayer, indicated at 526 includes K-coil peptide subunits, such as subunit 528, as described above. In the embodiment shown, each peptide subunit is coupled to the electrode surface via a tripeptide spacer, such as spacer 530 in subunit 528, which is itself attached to the electrode surface through a sulfhydryl linkage, as shown. The peptide, including the peptide spacer, is formed conventionally, e.g., by solid phase synthesis. The amount of peptide subunit in the monolayer is about 20 mole percent. The monolayer was formed according to the method described above with respect to FIGS. 5A,7A.

Presumably because of the positive charge imparted to the monolayer by the K-coil subunits, the monolayer shows relatively high conductance to negatively charged redox species, such as $Fe(CN)_6^{3-}$, as evidenced by a relatively high oxidation or reduction current with the redox species.

Figure 14:
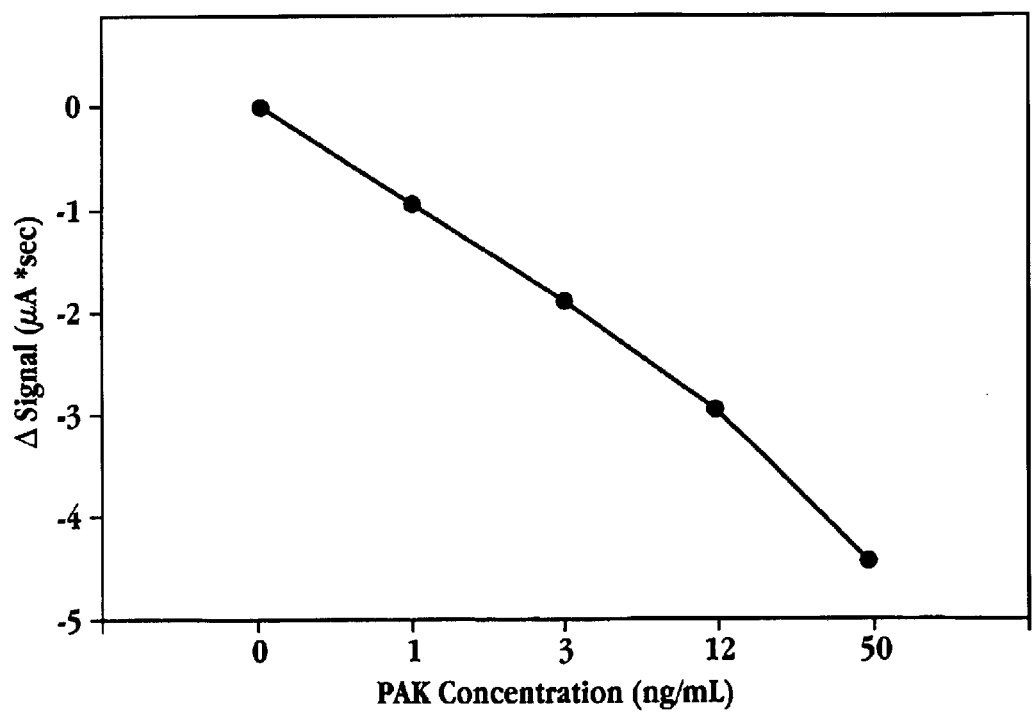
FIG. 14 is a plot showing change in biosensor signal, measured in nA*sec, as a function of PAK pilin peptide level in a competitive antibody binding assay.
Figure 16:
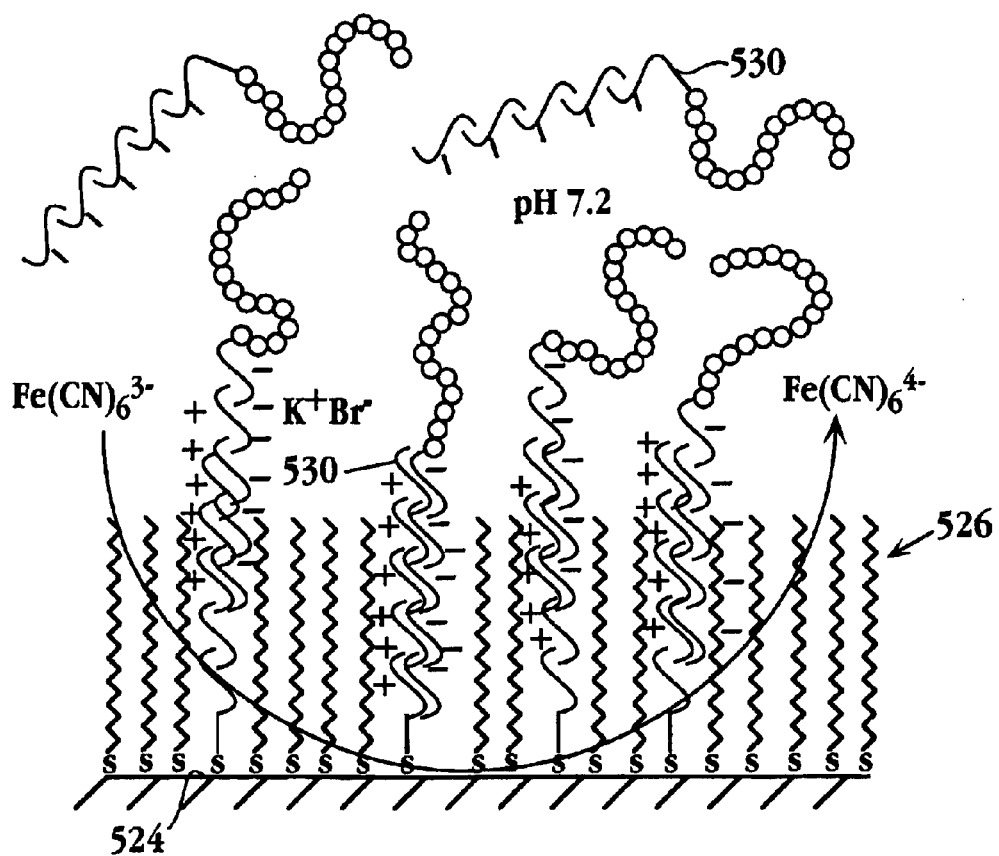
FIG. 16 illustrates the structure of an electrode monolayer having an embedded K-coil peptide subunit, in the presence of E-coil/PAK peptide conjugate.

FIG. 16 shows the same monolayer, but after addition of complementary, negatively charged E-coil subunits/PAK conjugate, such as indicated at 530. As shown, oppositely charged subunits pair to form charge-neutral heterodimers in the monolayer. This pairing is effective to reduce monolayer conductance substantially, as evidenced by the time-dependent fall in measured oxidation or reduction current in the presence of $Fe(CN)_6^{3-}$ ions (FIG. 16). A biosensor for determining PAK levels was constructed as described in Example 1 and demonstrates lower current at increased levels of PAK (FIG. 14). In Example 1, microtitre plates were coated with antibody to PAK protein receptor (PAK). Various levels of PAK were incubated in the wells with E-coil/PAK conjugate. At higher PAK concentration, more of the of the E-coil/PAK conjugate is free in solution due to competitive binding with the antibody. Originally, the surface of the K/C16 chip is positively charged allowing a high flow of negatively charged redox probe. At higher amounts of conjugate, the E-coil binds with the K-coil and neutralizes the positive charge by forming charge-neutral heterodimers which led to a decrease in conductance.

Figure 9:
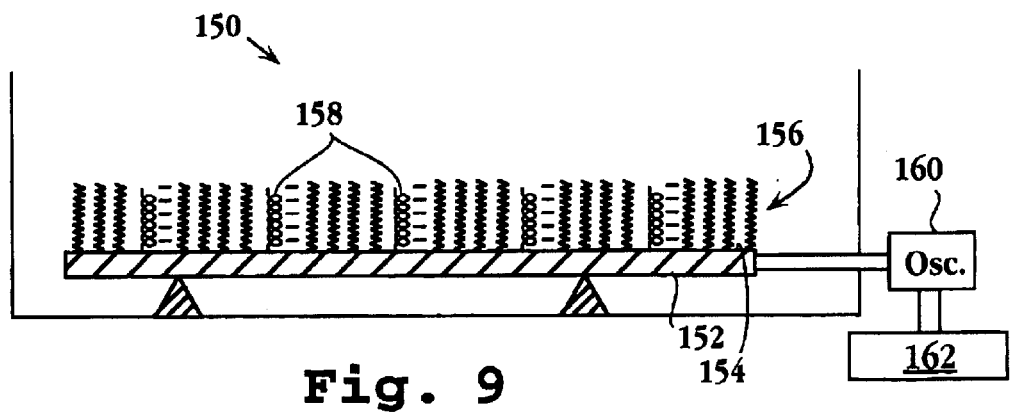
FIG. 9 shows elements of a gravimetric biosensor constructed in accordance with an embodiment of the invention.

FIG. 9 shows basic elements of a gravimetric biosensor 150 incorporating the novel biosensor surface of the invention. The biosensor has a piezoelectric crystal 90 whose biosensor surface is indicated at 154. HSP1 peptide 158 is anchored to the biosensor surface. A preferred embodiment includes a hydrocarbon monolayer 156 with HSP1 peptide 158 embedded therein.

Surface acoustic waves (SAW) are generated in the crystal by an oscillator 160. According to known piezoelectric biosensor principles, the change in mass in the biosensor surface resulting from heterodimer formation alters the frequency, resonance frequency, and wavelength of the SAW, and at least one of these wave characteristics is measured by a detector 162. The oscillator and detector collectively form detector means for detecting heterodimer formation. Details of crystal construction and associated detector means in gravimetric biosensors are given, for example, in U.S. Pat. Nos. 5,478,756 and 4,789,804, and in PCT application WO 96/02830.

Figure 10:
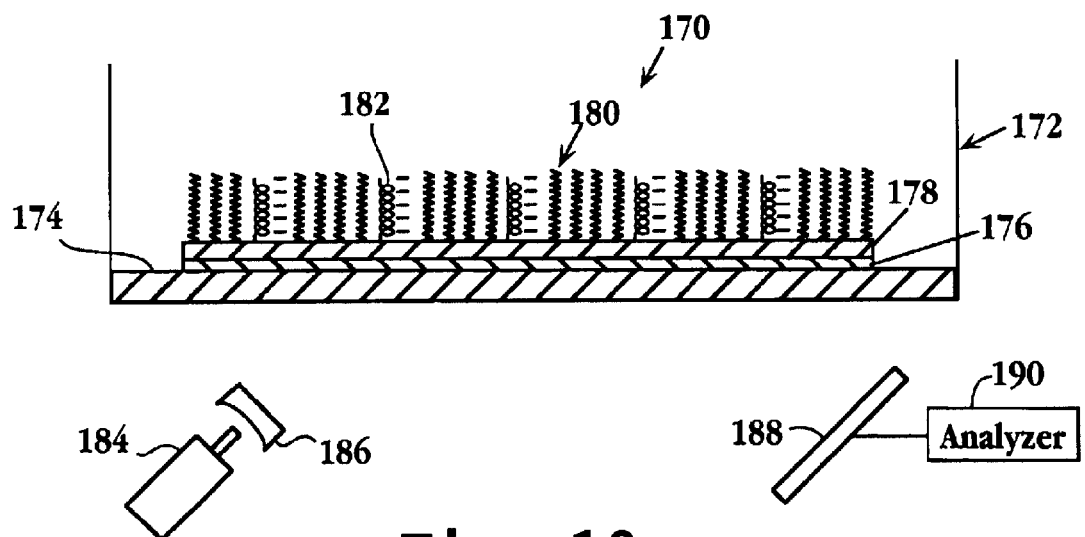
FIG. 10 shows elements of a surface plasmon resonance biosensor constructed in accordance with an embodiment of the invention.

FIG. 10 shows basic elements of a surface plasmon resonance (SPR) biosensor 170 incorporating the novel biosensor surface of the invention. A chamber 172 in the biosensor contains a waveguide composed of a dielectric film 174 (e.g., glass), a thin evaporated metal film 176 (e.g., chromium or titanium), and a thin film 178 (preferably of gold) constructed to support surface plasmon waves at the dielectric/metal film interface. The waveguide surface forms a biosensor surface having HSP1, such as E coil peptide 182, anchored thereon. A preferred embodiment includes a hydrocarbon monolayer 180 with HSP1 peptide 182 embedded therein.

A light source 184 directs a divergent light beam onto the biosensor surface through a lens 186. At some region along the length of the biosensor surface, the beam angle strikes the surface at an absorption angle at which absorption from the evanescent wave by surface plasmons occurs. The absorption angle will shift with changes in the composition of the material near the interface, that is, in response to binding events occurring on the monolayer surface.

The intensity of reflected light from each region along the biosensor surface is monitored by a photosensor 188 whose photosensing grid is matched to specific detector surface regions, and which is operatively connected to an analyzer 190. The light source and photosensor are also referred to herein as biosensor means.

In operation, the SPR absorption angle on the biosensor surface is measured before and after application of test sample, with the measured shift in angle being proportional to the extent of surface heterodimer formation.

Figure 11:
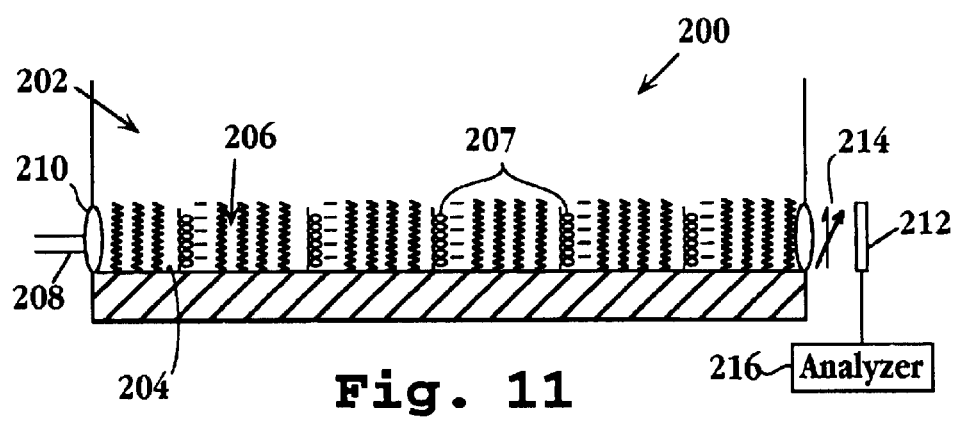
FIG. 11 shows elements of an optical biosensor constructed in accordance with an embodiment of the invention.

A variety of biosensor devices which rely on changes in the optical properties of a biosensor surface, in response to ligand/anti-ligand binding events, have been proposed. FIG. 11 shows basic elements of an optical biosensor apparatus 200 having an open chamber 202 and a biosensor surface 204 with HSP1 anchored, such as shown at 207. A preferred embodiment includes a hydrocarbon monolayer 206 with HSP1 peptide 207 embedded therein.

The detector means in the apparatus for detecting binding events on the biosensor surface includes a source 208 of polarized light and a lens system 210 for directing the light in a beam through the region of the monolayer. A photodetector 212 at the opposite side of the biosensor surface functions to measure intensity of light at a given polarization angle, through a polarization filter 214. Detection of heterodimer formation is based on the change of polarization angle and intensity of light transmitted by the monolayer in response to perturbation of the regular order of the monolayer by surface binding events. These changes are recorded by an analyzer 216 operatively connected to the photosensor.

Figure 12:
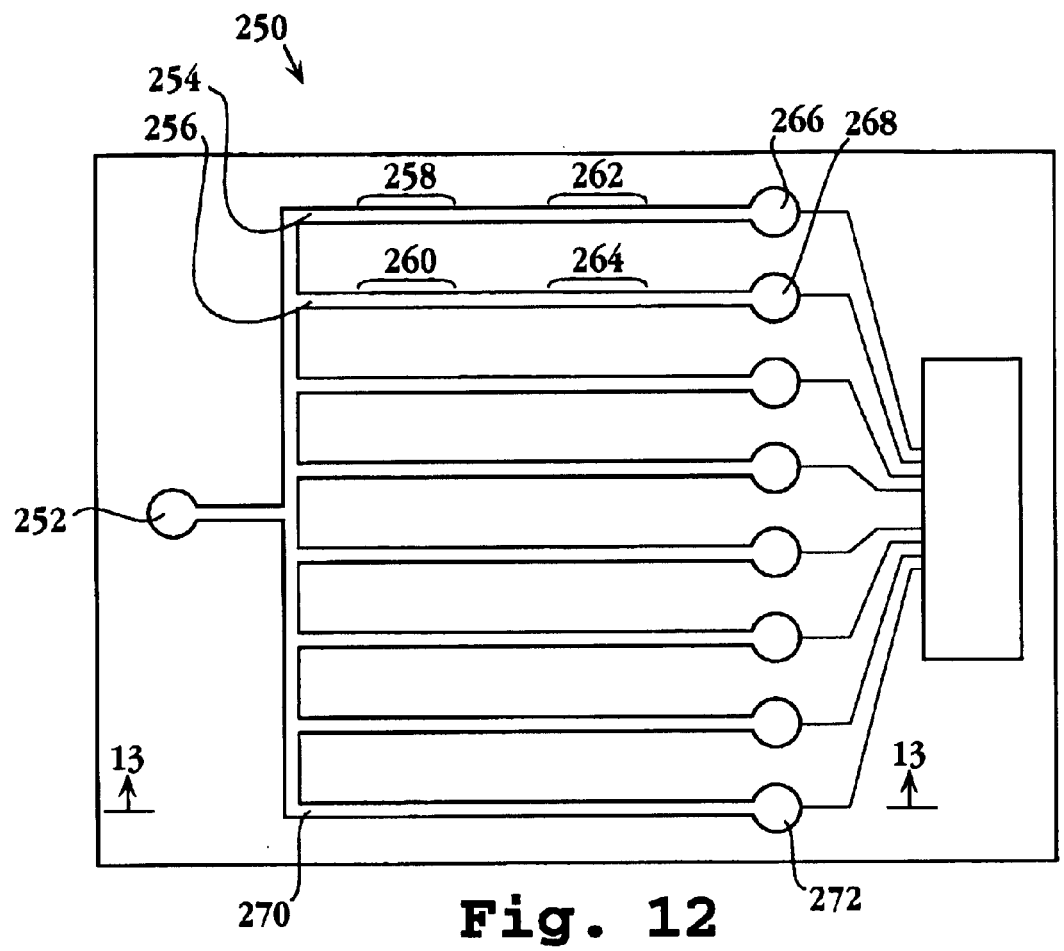
FIG. 12 is a simplified, partly schematic perspective view of a multi-analyte detection device in accordance with one aspect of the invention.
Figure 13:
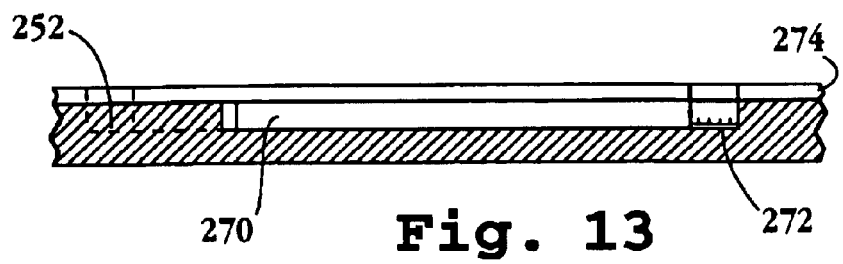
FIG. 13 is a view of a region of the device of FIG. 12 taken in the direction of arrows 13—13.

The detection devices described hereinabove are used in the detection of a single analyte. A multi-analyte detection device is readily constructed according to FIGS. 12 and 13 which show a multi-analyte detection device 250, and employing a biosensor selected form those as described hereinabove. The preferred device has a sample introduction area 252, such as a port, in liquid communication with each of a plurality of sample-flow pathways, such as flow paths 254, 256. Each sample flow path preferably is filled with a bibulous material and has a separate mixing zone, reaction zone, and biosensor for measuring a different analyte present in the test sample. Each mixing zone, such as 258, 260, contains a separate, releasably bound HSP2-analyte (or analyte analog) conjugate for each analyte being detected. Each reaction zone, such as 262, 264, contains an immobilized analyte-binding agent corresponding to the HSP2-analyte conjugate in the associated mixing zone. In one embodiment, all of the biosensors, such as 266, 268, contain HSP1 anchored to an electrochemical detection surface within a hydrocarbon monolayer as described hereinabove. In a preferred multi-analyte device, at least one of the sample flow paths, such as 270, is a control sample-flow pathway which lacks analyte HSP2 conjugate. The control sample-flow pathway is in liquid communication with background control biosensor 272 containing HSP1 anchored to a detection surface within a hydrocarbon monolayer, as described hereinabove. In the operation of this embodiment of the invention, test sample applied to the sample application region 252 flows into each of the separate sample-flow pathways and interacts with the respective reagents within each sample flow pathway in analogy to the dual lane electrochemical device illustrated in FIG. 1A. Each biosensor is connected to a detector for measuring the change in signal generated by each biosensor, in response to heteroduplex formation. The device preferably is provided with a lid 274.

The device preferably includes at least one biosensor which will be used as a positive control biosensor. This biosensor is not connected to the sample application port. It includes a fixed amount of HSP2-analyte conjugate pre-added, during manufacture of the positive control biosensor chamber, in an amount to give the limit of maximum expected response. Preferably, the positive control biosensor chamber contains the HSP2/analyte conjugate, redox species probe, and buffer-salts in a dried form which are rehydrated at the time of use of the device. For example, an aliquot of aqueous solution (e.g., albumin) can be contained in a reservoir (not shown). The control solution can be injected into the positive control biosensor chamber through a passage between the chamber and reservoir. The injection can be performed electronically, e.g., by a minipump or electroosmotic movement of solution through the passage, or manually, e.g., by depressing an injection means such as a flexible bulb associated with the reservoir (not shown).

More generally, the diagnostic device of the invention includes a reaction reagent effective to react with analyte to generate a solution form of a first coil-forming peptide of the type described above. The device further includes a biosensor, e.g., of the type described above, having a detection surface with surface-bound molecules of a second charged, coil-forming peptide capable of interacting with the first oppositely charged coil-forming peptide to form a stable α-helical coiled-coil heterodimer, where the binding of the first peptide to the second peptide, to form such heterodimer, is effective to measurably alter a signal generated by the biosensor, and a detector for measuring the change in a signal generated by the biosensor, in response to conjugate binding to the first charged, coil-forming peptide, as detailed above.

The reaction reagent in the device may include, for example, an immobilized or aggregated anti-analyte binding agent having a conjugate of the first coil peptide and analyte bound thereto, with the presence of analyte acting to release conjugate from the binding agent in proportion to the amount of analyte. The analyte, might be, for example, one of a large number of combinatorial species, where the assay is used for high-throughput screening for compounds effective to bind the binding agent.

Alternatively, the reaction reagent could be an immobilized enzyme-cleavable conjugate designed to cleave off and release coil peptide in the presence of an enzyme analyte. In still another embodiment, the first coil is produced recombinantly, either alone or as a fusion protein, in a recombinant system, and the presence of protein expression is detected by reaction of the recombinantly made coil protein with the biosensor. Other reagents and reagent formats in which the presence of analyte is effective to generate a first coil peptide in soluble form, such as are known to those skilled in the art, are also contemplated herein.

In the embodiment disclosed above, having a sample-introduction region and a sample-flow pathway between a sample-introduction region and the biosensor, the reaction reagent is disposed in the sample-flow pathway and includes a conjugate of the first coil-forming peptide and the analyte or an analyte analog, in a form releasable into the sample liquid, and an analyte-binding agent.

Also forming part of the invention, is a general assay method for detecting or quantitating an analyte present in a liquid sample. The method includes reacting the liquid sample with an analyte-reaction reagent, thereby to generate a solution form of a first coil-forming peptide having a selected charge and being capable of interacting with a second, oppositely charged coil-forming peptide to form a stable α-helical coiled-coil heterodimer. The first peptide so generated is contacted with a biosensor having a detection surface with surface-bound molecules of such second, oppositely charged coil-forming peptide, under conditions effective to form a stable α-helical coiled-coil heterodimer on said detection surface, where the binding of the solution form of the coil-forming peptide to the immobilized coil-forming peptide is effective to measurably alter a signal generated by the biosensor. The signal generated by the biosensor is then measured, to determine whether such coiled-coil heterodimer formation on said detector surface has occurred.

From the foregoing, it can be seen how various objects and advantages of the invention are met. The device of the invention can be formed under controlled manufacturing conditions consistent with microchip scale and photomask processes, to produce highly uniform and/or miniaturized and/or high-density array biosensor devices with sample introduction region, biosensor, and sample-flow pathway microfabricated on the substrate. The invention can be used to create multi-analyte assay surfaces by photomasking techniques that are capable of producing diagnostic devices having a plurality of unique sample-flow pathways, in fluid communication with highly reproducible biosensor elements.

After manufacture of a device with a plurality of identical biosensors, the plurality of sample-flow pathways can be readily adapted to a wide variety of analytes(s), by binding an HSP2 peptide conjugate in a releasable form within the mixing zone and by binding analyte-binding agent in an immobilized form within the reaction zone, carried out under relatively simple production conditions, thus combining both manufacturing precision at the initial production stage, and assay flexibility at the analyte and analyte-binding agent addition stage.

The invention is easily adapted to any of a variety of biosensor devices, such as those illustrated above.

EXAMPLE 1

Immunoassay for PAK Protein

In a competitive ELIZA format, anti-PAK mouse IgG (0.5 ug/well) was coated on a 96-well microtitre plate via an overnight incubation in 10 mM sodium carbonate buffer, pH, 9.5. The wells were blocked with 3% BSA in PBS, pH 7.4. A mixture of E-conjugate (E-coil/PAK protein conjugate) and various amount of PAK was prepared and incubated with the immobilized antibody at 37° C. for 2 hours. Aliquots removed from the plate after the incubation and applied to the K/C16 chip for analysis.

A biosensor chip (K/C16 chip) comprising C16 hydrocarbons and K-coil was inserted into a modified Hewlett Packard HPLC electrochemical-system. The sensor chip was equilibrated with a continuous flow of PBS and baseline response was taken by repeat injections (20 uL) of a probe solution (ferricyanide probe 1 mM in PBS). Measurement was taken at 180 mV versus a Ag/AgCl reference electrode.

Samples from the competitive ELIZA were injected using the autosampler. Each sample injection was followed by injections of the probe solution. The signal from the probe injections were integrated, averaged and reported.

The data are presented in FIG. 14 which shows the area under the peak (uA*sec) vs. concentration of PAK in the incubation.

Although the invention has been described with respect to particular devices and methods, it will be understood that various changes and modifications can be made without departing from the invention, as encompassed by the accompanying claims.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

It is claimed:

1. A method for detecting or quantitating an analyte present in a liquid sample, comprising
   reacting the liquid sample with an analyte-reaction reagent,
   by said reacting, generating a solution of a first coil-forming peptide having a selected charge for interacting with a second, oppositely charged coil-forming peptide to form a stable α-helical coiled-coil heterodimer,
   contacting the first coil-forming peptide generated by said reaction with a biosensor having a detection surface with surface-bound molecules of said second, oppositely charged coil-forming peptide, under conditions effective to form a stable α-helical coiled-coil heterodimer on said detection surface, where binding of the coil-forming peptide to the immobilized coil-forming peptide measurably alters a signal generated by the biosensor,
   measuring the signal generated by the biosensor to determine whether said coiled-coil heterodimer formation on said detector surface has occurred, and
   correlating said generated signal to the presence of the analyte in the sample.

2. The method of claim 1, wherein said analyte is a ligand, and said reacting includes mixing the analyte with a conjugate of the first coil-forming peptide and the analyte or an analyte analog, and reacting the analyte and conjugate with an analyte-binding anti-ligand agent, such that the amount of unbound conjugate generated is inversely proportional to the amount of analyte.

3. The method of claim 2, wherein the analyte-bound agent is immobilized.

4. The method of claim 1, wherein said analyte is a ligand, and said reacting includes mixing the analyte with a conjugate of the first coil-forming peptide and the analyte or an analyte analog, under conditions that the conjugate is displaced from an immobilized analyte-binding anti-ligand agent when analyte is present.

5. The method of claim 1, wherein the analyte is an enzyme and said reacting enzymatically releases said second coil-forming peptide in soluble form when analyte is present.

6. The method of claim 1, wherein the biosensor is an electrochemical biosensor that includes a conductive detection surface, a monolayer composed of hydrocarbon chains anchored at their proximal ends to the detection surface, and the second charged coil-forming peptide also anchored to said surface, where binding of the first peptide to the second peptide, to form said heterodimer, measurably alters current flow across the monolayer mediated by a redox ion species in an aqueous solution in contact with the monolayer, relative to electron flow observed when the second peptide alone is present.

7. The method of claim 6, wherein the redox ion species has a charge equal to said second coil-forming peptide, and binding of the first peptide to the second peptide enhances ion-mediated current flow across said monolayer.

8. The method of claim 6, wherein the redox ion species is $Fe(CN)_6^{3-}$, if the charge of said first coil-forming peptide is negative, and $Ru(NH_3)_6^{3+}$, if the charge of said first coil-forming peptide is positive.

9. The method of claim 6, wherein the redox ion species has a charge opposite that of said second coil-forming peptide, and binding of the first peptide to the second peptide reduces ion-mediated current flow across said monolayer.

10. The method of claim 6, wherein the redox ion species is $Fe(CN)_6^{3-}$, if the charge of said first coil-forming peptide is positive, and $Ru(NH_3)_6^{3+}$, if the charge of said first coil-forming peptide is negative.

* * * * *

SEQUENCE LISTING

```
<160> NUMBER OF SEQ ID NOS: 2

<210> SEQ ID NO 1
<211> LENGTH: 35
<212> TYPE: PRT
<213> ORGANISM: Artificial Sequence
<220> FEATURE:
<223> OTHER INFORMATION: peptide
<220> FEATURE:
<221> NAME/KEY: VARIANT
<222> LOCATION: (1)...(35)
<223> OTHER INFORMATION: EE peptide

<400> SEQUENCE: 1

Glu Val Glu Ala Leu Gln Lys Glu Val Ser Ala Leu Glu Lys Glu Val
 1               5                  10                  15

Ser Ala Leu Glu Cys Glu Val Ser Ala Leu Glu Lys Glu Val Glu Ala
            20                  25                  30

Leu Gln Lys
        35

<210> SEQ ID NO 2
<211> LENGTH: 35
<212> TYPE: PRT
<213> ORGANISM: Artificial Sequence
<220> FEATURE:
<223> OTHER INFORMATION: peptide
<220> FEATURE:
<221> NAME/KEY: VARIANT
<222> LOCATION: (1)...(35)
<223> OTHER INFORMATION: KK peptide

<400> SEQUENCE: 2

Lys Val Glu Ala Leu Lys Lys Val Ser Ala Leu Lys Glu Lys Val
 1               5                  10                  15

Ser Ala Leu Lys Cys Lys Val Ser Ala Leu Lys Glu Lys Val Glu Ala
            20                  25                  30

Leu Lys Lys
        35
```